US010953082B2

(12) United States Patent
Rhee et al.

(10) Patent No.: US 10,953,082 B2
(45) Date of Patent: Mar. 23, 2021

(54) PREPARATION OF FLAGELLIN VACCINE ADJUVANT-BASED VACCINE TO INDUCE PRODUCTION OF ANTIBODY RECOGNIZING CONFORMATION OF ANTIGENS, AND APPLICATION THEREOF

(71) Applicants: Joon Haeng Rhee, Gwangju (KR); Shee Eun Lee, Gwangju (KR); Kwangjoon Jeong, Gwangju (KR); Sang Chul Park, Gyeonggi-Do (KR); Wenzhi Tan, Jeollanam-Do (KR)

(72) Inventors: Joon Haeng Rhee, Gwangju (KR); Shee Eun Lee, Gwangju (KR); Kwangjoon Jeong, Gwangju (KR); Sang Chul Park, Gyeonggi-Do (KR); Wenzhi Tan, Jeollanam-Do (KR)

( * ) Notice: Subject to any disclaimer, the term of this patent is extended or adjusted under 35 U.S.C. 154(b) by 28 days.

(21) Appl. No.: 16/312,510

(22) PCT Filed: Nov. 17, 2016

(86) PCT No.: PCT/KR2016/013303
§ 371 (c)(1),
(2) Date: Jan. 17, 2019

(87) PCT Pub. No.: WO2017/222120
PCT Pub. Date: Dec. 28, 2017

(65) Prior Publication Data
US 2019/0160163 A1     May 30, 2019

(30) Foreign Application Priority Data

Jun. 21, 2016 (KR) .................. 10-2016-0077414

(51) Int. Cl.
| A61K 39/02 | (2006.01) |
| C07K 14/47 | (2006.01) |
| A61K 39/00 | (2006.01) |
| A61K 39/12 | (2006.01) |
| A61P 25/28 | (2006.01) |
| A61K 9/00 | (2006.01) |
| A61P 31/18 | (2006.01) |

(52) U.S. Cl.
CPC .......... *A61K 39/107* (2013.01); *A61K 9/0019* (2013.01); *A61K 39/00* (2013.01); *A61K 39/02* (2013.01); *A61K 39/12* (2013.01); *A61P 25/28* (2018.01); *A61P 31/18* (2018.01); *C07K 14/47* (2013.01); *A61K 2039/51* (2013.01); *A61K 2039/6075* (2013.01)

(58) Field of Classification Search
None
See application file for complete search history.

(56) References Cited

U.S. PATENT DOCUMENTS

2008/0050383 A1    2/2008  Sigurdsson et al.

FOREIGN PATENT DOCUMENTS

| JP | 2014-530597 A | 11/2014 | |
| WO | WO 2004/007547 | * 1/2004 | ............. C07K 14/47 |
| WO | WO 2004/007722 | * 1/2004 | ............. C12N 15/12 |
| WO | WO-2004/007722 A2 | 1/2004 | |
| WO | WO-2004/007722 A3 | 3/2004 | |
| WO | WO-2008/097016 A1 | 8/2008 | |
| WO | WO 2013/041962 | * 3/2013 | ............. C07K 16/18 |

OTHER PUBLICATIONS

Machine translation of KR20100114620; downloaded Jun. 15, 2020 (Year: 2020).*
Press release by Alzforum, published Apr. 15, 2020; downloaded from the website https://www.alzforum.org/news/conference-coverage/active-tau-vaccine-hints-slowing-neurodegeneration; 7 pages total (Year: 2020).*
Julie Ries, published online Jun. 12, 2019; downloaded from https://www.healthline.com/health-news/dont-bet-on-an-alzheimers-vaccine-anytime-soon#Lengthy-wait-time; 13 pages total (Year: 2019).*
Kontsekova, E. et al, "First-in-man tau vaccine targeting structural determinants essential for pathological tau-tau interaction reduces tau oligomerisation and neurofibrillary degeneration in an Alzheimer's disease model", Alzheimer's Research & Therapy 2014.
Shee Eun Lee et al, "A Bacterial Flagellin, *Vibrio vulnificus* FlaB, Has a Strong Mucosal Adjuvant Activity to Induce Protective Immunity", Infection and Immunity, Jan. 2006.
Verma, V. et al, "Norovirus (NoV) specific protective immune responses induced by recombinant P dimer vaccine are enhanced by the mucosal adjuvant FlaB", Journal of Translation Medicine, 2016.
NCBI, GenBank accession No. AAS91779.2 (Jun. 10, 2016).
NCBI Reference sequence: XM_005257371.4 (Jun. 6, 2016).
NCBI Reference sequence: WP_011079824.1 (May 15, 2013).
NCBI, PDB: 2OBR_A (Oct. 10, 2012).
NCBI, Genbank accession No. KJ407076.1 (Sep. 17, 2015).
International Search Report from corresponding PCT Application No. PCT/KR2016/013303.
Hong, et al. (2012) "Intranasal administration of a flagellin-adjuvanted inactivated influenza vaccine enhances mucosal immune responses to protect mice against lethal infection." *Vaccine*, 30:466-474.
Lee, et al. (2015) "Tetanus toxin fragment C fused to flagellin makes a potent mucosal vaccine." Clin. Exp. Vaccine Res., 4:59-67.
Nguyen, et al. (2011) "Intranasal immunization with recombinant PspA fused with a flagellin enhances cross-protective immunity against *Streptococcus pneumoniae* infection in mice." *Vaccine*; 29:5731-57390.

(Continued)

*Primary Examiner* — Christina M Borgeest
(74) *Attorney, Agent, or Firm* — Harness, Dickey & Pierce, P.L.C.

(57) ABSTRACT

The present invention provides a vaccine composition for use in neurodegenerative diseases and an infectious virus vaccine composition for inducing an antibody recognizing the conformation of antigens. The vaccine composition of the present invention induces the production of an antibody recognizing the conformation of antigens. The antibody recognizing the conformation of antigens has high specificity for an antigen, and thus can be useful for ameliorating, preventing or treating diseases.

3 Claims, 17 Drawing Sheets

Specification includes a Sequence Listing.

(56) References Cited

OTHER PUBLICATIONS

Notice of Reasons for Rejection of Japanese Patent Application No. 2019-520341 dated Dec. 3, 2019.
Ming Tan & Xi Jiang (2014) "Vaccine against norovirus.", *Human Vaccines & Immunotherapeutics*, 10:6, 1449-1456, DOI: 10.4161/hv.28626.
Giacobini, E., et al.; "Alzheimer disease therapy—moving from amyloid-β to tau", Nat. Rev. Neurol., 9, 667-686, 2013.
Extended European Search Report from corresponding European Patent Application No. 16906395.5, dated Apr. 21, 2020.
Notice of Allowance dated Jun. 11, 2019 in Korean Patent Application No. KR 10-2018-0139971.

* cited by examiner

PREPARATION OF FLAGELLIN VACCINE ADJUVANT-BASED VACCINE TO INDUCE PRODUCTION OF ANTIBODY RECOGNIZING CONFORMATION OF ANTIGENS, AND APPLICATION THEREOF

CROSS-REFERENCE TO RELATED APPLICATIONS

This application is a national phase application of PCT Application No. PCT/KR2016/013303, filed on 17 Nov. 2016, which claims the benefit and priority to Korean Patent Application No. 10-2016-0077414, filed on 21 Jun. 2016. The entire disclosures of the applications identified in this paragraph are incorporated herein by references.

FIELD

The present invention relates to a production of flagellin-adjuvanted vaccine to induce the production of conformer antigen recognizing antibodies and an application thereof.

BACKGROUND

Antibodies are substances that specifically recognize and bind to antigens to cause antigen-antibody interactions, thereby inducing protective immune responses. In the immune system, immunoglobulins, which recognize and specifically bind to cancers and other autologous internal antigens as well as external antigens, such as bacteria or viruses, to simultaneously perform neutralization or opsonic phagocytosis, are called immune antibodies. In general, those called antibodies are immune antibodies that specifically recognize and bind to particular antigens.

Antibody production by B lymphocytes/plasma cells is facilitated by allowing antigen presenting cells to phagocytize and digest exogenous or endogenous antigens and to transfer the antigenic moiety to T lymphocytes. After a particular fraction of B cell clones recognizing corresponding antigens are selected and expanded through initial infection, corresponding cells differentiate into plasma cells to form antibodies. Due to the nature of the immune response, the rate and amount of antibody formation during re-infection are explosively increased compared with the initial infection. This is the currently known theoretical basis for vaccination for the prevention of infectious diseases and the like or for the immunotherapy of particular types of cancer (cancers highly expressing cancer antigens).

The currently known mechanisms of elimination of recognized antigens through antigen-antibody binding are as follows. Of the mechanisms, the most widely known mechanism is opsonic phagocytosis that promotes phagocytosis by phagocytes. Alternatively, antigen-dependent cell-mediated cytotoxicity (ADCC) by natural killer cells is known to play a very important role in the elimination of the infected cells by intracellular pathogens or malignant cells labeled with specific antigens. Finally, the classical complement activation pathway induced by antigen-antibody complex formation is one of the strongest countermeasures by which the human immune system responds to pathogen infection and the like.

Since the presence of antibodies has been identified, efforts have been made to utilize antigen-antibody responses for the prevention or treatment of various disease groups including infectious diseases as well as tumors. Antigen-antibody responses are known to have very high specificity ($10^{-12}$ mol/L or lower) among various in vivo and in vitro biological binding responses, and it was expected that therapies having safer and higher therapeutic effects would be developed by using the antigen-antibody responses. With the development of cancer therapy techniques using monoclonal antibodies in the late 1990s, monoclonal antibody-based drugs have come to account for 80% or more of the top 10 drugs for which markets were approved by the US FDA since 2006. In particular, several immunotherapies including antibody therapy are receiving attention as new therapeutic methods for neoplastic diseases, such as cancers. Since an anti-PD-1 monoclonal antibody, as an immune checkpoint inhibitor, was approved to be marketed in 2014, immunotherapies have emerged as the most popular and effective modality in cancer treatment.

For the success of such antibody-based immunotherapy, the selection of appropriate antigens and the production of optimized antibodies are essential requirements. That is, the finding of target antigens having high selectivity and specificity in particular diseases as well as the development of techniques for producing antibodies specifically recognizing and binding to the target antigens is the most important step in determining the success or failure of antibody-based immunotherapy.

Until now, antibodies may be largely immunologically divided into two types according to the characteristics of antigens that can be recognized and bound by antibodies. First-type antibodies are "linear epitope recognizing antibodies", which recognize and bind to sequences of oligopeptides (8-12 amino acids) or carbohydrates, nucleotides digested or presented on foreign antigens. And the second-type antibodies are "structure recognizing antibodies or conformer antigen recognizing antibodies", which recognize and bind to three-dimensional structures inherent to specific antigens. When the production of antibodies to particular antigens is induced, most of the antibodies produced are "linear epitope recognizing antibodies", which are classified in the first-type category. However, purportedly, compared with sequence recognizing antibodies that can recognize sequences of antibodies and bind to the antibodies, antibodies recognizing structures of antigens, that is, conformer antigen recognizing antibodies do not only have higher specificity to antigens, but are also able to exhibit binding strength to antigens showing particular structural characteristics, and therefore the conformer antigen recognizing antibodies can more highly induce protective immunological responses against similar structures composed of different amino acids, thereby providing broadly protective antigen-antibody responses.

Despite of the development of preventive vaccines against various infectious diseases, it remains as distant future to develop vaccines for many infectious diseases including human immunodeficiency virus (HIV) and respiratory syncytial virus (RSV), neoplastic diseases, such as cancer, and neurodegenerative diseases, such as Alzheimer's disease and Parkinson's syndrome by tauopathy, and neurodegenerative diseases, such as prion-related diseases, are still in the very distant future. Moreover, in case of the influenza vaccines, it still has great disadvantages in that users have to be vaccinated every year due to the frequent antigenic variation. And the current vaccines can show no preventive effect in case of the antigenic mismatch between predicted and actual strains. This teaches us that there is still a major obstacle to the production of antibodies induced by using current vaccine development techniques. In other words, most of the antibodies induced by vaccination using artificial antigens produced using current techniques are "linear epitope recognizing antibodies", which will inevitably confer limited range of protection.

It is thought that broadly neutralizing antibody induction may be a prerequisite for successful vaccination in the aforementioned HIV vaccines. That is, the success of AIDS vaccines may also ultimately depend on whether or not structure recognizing antibodies for envelope glycoprotein trimers are induced. Besides, efficacious RSV or universal influenza vaccines are also required to induce conformer recognizing antigen-antibody reactions. Furthermore, the effective and efficacious induction of conformer antigen recognizing antibodies should be very crucial for successful immunotherapy against endogenous diseases, such as neoplastic diseases and neurodegenerative diseases, as well as infectious diseases.

The tauopathy, which was directly related to pathogenic alteration of normal tau protein, is known as a most frequent and important cause of Alzheimer's disease and other neurodegenerative diseases. It caused by pathologic hyperphosphorylation and subsequent aggregation of pathologic form of endogenous monomeric tau protein. The monomeric tau is essential for maintaining the robustness of neuronal axons. By the way, after hyperphosphorylation due to any physicochemical stimuli, the monomeric tau aggregates and forms the paired helical filaments (PHFs). These pathologic alterations of tau protein are known as a one of most important cause of tauopathy and pathological damage to neurons. Similar pathogenic mechanism is not limited to Alzheimer's disease, but also occurs in several series of neurodegenerative and neurological diseases, such as Creutzfeldt-Jakob disease by infectious prions and Parkinson's disease by pathologic aggregation of alpha synucleins. Therefore, the induction of conformer antigen recognizing antibodies that selectively and specifically recognize and bind to pathological forms of endogenous protein aggregates should contribute to successful and safe immunotherapies against various pathologic protein aggregation diseases.

SUMMARY

Technical Problem

The present inventors have endeavored to produce a flagellin-based vaccine composition for inducing the production of conformer antigen recognizing antibodies. As a result, the present inventors have prepared a vaccine composition capable of alleviating, preventing, and treating Alzheimer's disease by preparing a recombinant protein of a disease-mediated region, which is a repeated domain (RD) playing an important role for the pathologic aggregate formation, in tau (τ) protein and FlaB protein, which is a flagellar structural component of *Vibrio vulnificus* and show the immune sera suppress aggregation of pathologic tau (τ) protein. Also the present inventors have prepared a norovirus vaccine composition by preparing a recombinant protein of P domain, which is antigenic domain of norovirus envelope protein and FlaB protein, which is a flagellar structural component of *Vibrio vulnificus*, and thus the present inventors completed the present invention.

Therefore, an aspect of the present invention is to provide a recombinant protein including an RD of tau (τ) protein and FlaB protein derived from *Vibrio vulnificus*.

Another aspect of the present invention is to provide a vaccine composition for the prevention or immunotherapy of a neurodegenerative disease.

Still another aspect of the present invention is to provide a codon-optimized nucleotide for coding an RD of tau (τ) protein.

Another aspect of the present invention is to provide a recombinant protein including P domain of norovirus and FlaB protein derived from *Vibrio vulnificus*.

Still another aspect of the present invention is to provide a vaccine composition for the prevention of norovirus.

Another aspect of the present invention is to provide a method for preparing a vaccine composition for inducing a conformer antigen recognizing antibody.

Technical Solution

In accordance with an aspect of the present invention, there is provided a vaccine composition for a neurodegenerative disease to induce a conformer antigen recognizing antibody, the vaccine composition containing, as an active ingredient, a recombinant protein including: (a) a repeated domain (RD) of tau (τ) protein; and (b) FlaB protein derived from *Vibrio vulnificus*.

In accordance with another aspect of the present invention, there is provided a vaccine composition for an infectious virus to induce a conformer antigen recognizing antibody, the vaccine composition containing, as an active ingredient, a recombinant protein including: (a) a capsid protein of the infectious virus; and (b) FlaB protein derived from *Vibrio vulnificus*.

The present inventors have endeavored to produce a flagellin-based vaccine composition for inducing the production of a conformer antigen recognizing antibody. As a result, the present inventors have prepared a vaccine composition capable of alleviating, preventing, and treating Alzheimer's disease by preparing a recombinant protein of a disease-mediated region, that is, a repeated domain (RD) by which hyper phosphorylation is induced, in tau (τ) protein and FlaB protein, which is a flagellar structural component of *Vibrio vulnificus* and conferring the recombinant protein to suppress hyper phosphorylation and aggregation of tau (τ) protein, which is an endogenous protein causing Alzheimer's disease, and the present inventors have prepared a norovirus vaccine composition by preparing a recombinant protein of P domain, which is a membrane domain of norovirus and FlaB protein, which is a flagellar structural component of *Vibrio vulnificus*.

In the present invention, a vaccine composition for a neurodegenerative disease induces the production of a conformer antigen recognizing antibody, the vaccine composition containing, as an active ingredient, a recombinant protein including: (a) a repeated domain (RD) of tau (τ) protein; and (b) FlaB protein derived from *Vibrio vulnificus*.

As used herein, the term "tau protein" refers to a microtubule-associated protein (MAP), which is mainly expressed in the central nervous system, especially, axons of neurons and serves to stabilize microtubules.

Although there are a variety of theories about etiological causes of many neurodegenerative diseases including Alzheimer's disease, the current most widely accepted theory is that the abnormal occurrence of endogenous proteins (by hyperphosphorylation or the like), apoptosis of neurons due to the aggregation of endogenous proteins, overactivation of glial cells, and the like cause chronic inflammation responses and the resulting destruction of brain tissues.

It has been revealed that a repeated domain (hereinafter, RD), located between the $262^{nd}$ to $356^{th}$ amino acids of the tau protein, is a domain involved in the phosphorylation of the tau protein. The hyperphosphorylation of the tau protein is controlled by the balanced regulation of intracellular kinase and phosphatase in a normal state, but the hyperphosphorylation of the tau protein is induced when some endogenous and exogenous stimuli cause problems in such a regulation mechanism. Compared with the original nature thereof having high solubility in water, the hyperphosphorylated tau protein has severely low solubility in water and self-aggregates. The aggregated hyperphosphorylated tau protein is observed as a neurofibrillary tangle (hereinafter, NFT) in autopsy brain samples from Alzheimer's patients. The aggregated tau protein is mainly distributed in axons of neurons in early stages, inhibiting the stability of axonal microtubules, thereby hindering normal actions of cells and causing apoptosis of neurons. However, the severe aggregation of tau protein spreads even to surrounding neurons and glia, causing widespread destruction of brain tissues, such as apoptosis of corresponding cells as well as surrounding cells and chronic inflammation due to activity of microglia, resulting in neurodegenerative diseases.

In the present invention, a recombinant protein is prepared using an RD located between the $262^{nd}$ to $356^{th}$ amino acids of the tau protein, and the function of the recombinant protein as an antigen (or immunogen) is investigated.

As used herein, the term "conformer antigen recognizing antibody" refers to a structure recognizing antibody, which recognizes a three-dimensional conformation inherent to an antigen and binds to the antigen (A K Abbas & A H Lichtman, Cellular and molecular immunology, 6th edition, 2003, Elsevier, p. 59).

As used herein, the term "antigen" refers to a substance, which is an RD protein derived from the above-described tau protein and stimulates the immune system to induce an immune response specific to a living body. The term "antigen" may be used interchangeably with the term "immunogen" herein.

The recombinant protein may be prepared by various methods known in the art. For example, the recombinant protein may be prepared through a gene cloning method.

According to an embodiment of the present invention, the RD has the amino acid sequence of SEQ ID NO: 3.

The RD is coded by the nucleotide sequence of SEQ ID NO: 5, which is a codon-optimized nucleotide sequence for expression in *E. coli*.

For the preparation of the recombinant protein using *E. coli*, the nucleotide sequence of the RD of the tau protein is codon-optimized to be suitable for expression in *E. coli*. The human-derived RD was converted to have codons suitable for *E. coli* in order to allow the human-derived RD to be highly expressed in *E. coli*. In a gene sequence that has undergone codon optimization, only the nucleotide sequence is converted, but the amino acid sequence is not converted.

The nucleotide sequence used in the present invention is construed to include the foregoing sequence as well as a nucleotide sequence showing substantial identity with respect to the nucleotide sequence. The term "substantial identity" means that when the present nucleotide sequence and any different sequence are aligned to correspond to each other as much as possible and the aligned sequences are analyzed using an algorithm that is ordinarily used in the art, the nucleotide sequences show at least 80% homology, preferably at least 90% homology, and most preferably at least 95% homology. Methods of alignment for sequence comparison are known in the art. Various methods and algorithms for alignment are disclosed in Smith and Waterman, Adv. Appl. Math. 2:482 (1981); Needleman and Wunsch, J. Mol. Bio. 48:443 (1970); Pearson and Lipman, Methods in Mol. Biol. 24: 307-31 (1988); Higgins and Sharp, Gene 73:237-44 (1988); Higgins and Sharp, CABIOS 5:151-3 (1989); Corpet et al., Nuc. Acids Res. 16:10881-90 (1988); Huang et al., Comp. Appl. Bio Sci. 8:155-65 (1992) and Pearson et al., Meth. Mol. Biol. 24:307-31 (1994). The NCBI Basic Local Alignment Search Tool (BLAST) (Altschul et al., J. Mol. Biol. 215:403-10 (1990)) is available from NCBI (National Center for Biological Information), and on the Internet, may be used in connection with sequence analysis programs, such as blastp, blasm, blastx, tblastn, and tblastx. BLAST can be accessed at www.ncbi.nlm.nih.gov/BLAST/. The sequence homology comparison method using such a program can be confirmed atwww.ncbi.nlm.nih.gov/BLAST/blast help.html.

The FlaB protein constituting the recombinant protein is an immunoadjuvant derived from *Vibrio vulnificus*.

According to an embodiment of the present invention, the FlaB protein has the amino acid sequence of SEQ ID NO: 2.

As verified in the examples below, the recombinant protein has the amino acid sequence of SEQ ID NO: 7, and is coded by the nucleotide sequence of SEQ ID NO: 6.

The composition of the present invention contains other drugs or immunoadjuvants, and thus can provide additional immunostimulatory effects. For example, the composition of the present invention contains aluminum salts ($Al(OH)_3$ and $AlPO_4$), squalene, sorbitan, Polysorbate 80, CpG, liposomes, cholesterol, monophosphoryl lipid A (MPL), surfactins, bacteria-derived substances, cytokines, hormones, polyanions, polyacrylic materials, carriers, living vectors, mineral oils, *Vibrio cholera*-derived cholera toxin and glucopyranosyl lipid A (GLA), but is not limited thereto.

As verified in the examples below, the vaccine composition for a neurodegenerative disease of the present invention is a vaccine composition for oral or parenteral administration, the composition containing, as an active ingredient, a recombinant protein including: (a) RD of tau (τ) protein; and (b) FlaB protein derived from *Vibrio vulnificus*.

According to an embodiment of the present invention, the composition is for mucosal, subcutaneous, intracutaneous, percutaneous or intramuscular immunization.

According to another embodiment of the present invention, the composition is for mucosal immunization.

The mucosal immunization includes oral immunization, intranasal immunization, sublingual immunization, rectal immunization and vaginal immunization, but is not limited thereto.

The hyperphosphorylation of the tau protein forms aggregates, and the aggregated hyperphosphorylated tau protein is observed as a neurofibrillary tangle in autopsy brain samples from Alzheimer's patients. The aggregated tau protein is mainly distributed in axons of neurons in early stages, inhibiting the stability of axonal microtubules, thereby hindering normal actions of cells and causing apoptosis of neurons. Severe aggregation of tau protein causes widespread destruction of brain tissues, such as apoptosis of surrounding cells and chronic inflammation due to activity of microglia, thus expressing symptoms of neurodegenerative diseases.

According to an embodiment of the present invention, the vaccine composition induces the production of an antibody specific to tau protein aggregates.

According to another embodiment of the present invention, the antibody suppresses the aggregation of tau protein.

An antibody produced by administering the vaccine composition of the present invention to a subject suppresses the aggregation of tau protein.

According to another embodiment of the present invention, the antibody promotes opsonic phagocytosis.

As used herein, the term "opsonic phagocytosis" means phagocytosis by opsonins, which help the phagocytosis of leucocytes.

The vaccine composition of the present invention is a vaccine composition for the alleviation, prevention, or treatment of a neurodegenerative disease.

According to an embodiment of the present invention, the neurodegenerative disease is a disease selected from the group consisting of Alzheimer's disease, tauopathy, dementia, Huntington's disease, Parkinson's disease, amyotrophic lateral sclerosis, memory loss, myasthenia gravis and prion-related diseases.

According to another embodiment of the present invention, the tauopathy include argyrophilic grain dementia, corticobasal degeneration, dementia pugilistica, neurofibrillary tangles, frontotemporal dementia with parkinsonism linked to chromosome 17, Hallervorden-Spatz disease, myotonic dystrophy, Niemann-Pick disease type C, Pick's disease, postencephalitic parkinsonism, progressive subcortical gliosis, progressive supranuclear palsy, subacute sclerosing panencephalitis, and prion-causing diseases, such as Creutzfeldt-Jakob disease.

A pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oils. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and agents are described in detail in *Remington's Pharmaceutical Sciences* (19th ed., 1995).

A suitable dose of the pharmaceutical composition of the present invention may vary depending on various factors, such as the method for formulation, the manner of administration, the patient's age, body weight, gender, morbidity, and diet, the time of administration, the excretion rate, and the response sensitivity. Meanwhile, the oral dose of the pharmaceutical composition of the present invention is preferably 0.001-100 mg/kg (body weight) per day.

The pharmaceutical composition of the present invention may be formulated in a unit dosage form or into a multi-dose container using a pharmaceutically acceptable carrier and/or excipient according to a method that is easily conducted by a person having ordinary skills in the art to which the present invention pertains. Here, the dosage form may be a solution in an oily or aqueous medium, a suspension, an emulsion, an extract, a powder, granules, a tablet, or a capsule, and may further contain a dispersant or a stabilizer.

According to another aspect of the present invention, the present invention provides the nucleotide sequence of SEQ ID NO: 5, which is a nucleotide sequence codon-optimized to code the RD of the tau (τ) protein.

Since the nucleotide of the present invention is a nucleotide constituting the recombinant protein, descriptions of content common to the nucleotide and the recombinant protein are omitted in order to avoid excessive complication of the specification.

According to still another aspect of the present invention, the present invention provides a vaccine composition for an infectious virus, the vaccine composition containing, as an active ingredient, a recombinant protein including: (a) a capsid protein of the infectious virus; and (b) FlaB protein as a flagellar structural component of *Vibrio vulnificus*.

According to an embodiment of the present invention, the infectious virus is norovirus, human immunodeficiency virus, or respiratory syncytial virus.

According to another embodiment of the present invention, the capsid protein of the infectious virus is P domain of norovirus.

The norovirus is an enteritis-inducing virus, and it has been reported that approximately 50% of food poisoning causes result from norovirus and 96% of viral gastroenteritis cases are caused by norovirus (Centers for Disease Control and Prevention, Surveillance for Norovirus Outbreaks). The nucleotide sequence of the capsid gene of norovirus is closely associated with a viral antigen. It is known that the capsid protein of norovirus is largely composed of three protein domains: S, P1, and P2. The S domain is a conserved region, and antigenic diversity occurs according to the change in the protein sequence between P1 and P2 (Hardy, M. E., 2005).

The P domains include the 222nd to 539th amino acids including P1 and P2 domains of virus-like particles (VLP) of norovirus. The P domain has the amino acid sequence of SEQ ID NO: 13, and is coded by the nucleotide sequence of SEQ ID: 12.

As verified in the examples below, the recombinant protein has the amino acid sequence of SEQ ID NO: 15, and is coded by the nucleotide sequence of SEQ ID NO: 14.

The vaccine composition induces the production of an antibody specifically recognizing a structure of norovirus.

The vaccine composition is a vaccine composition for oral or parenteral administration.

According to an embodiment of the present invention, the composition is for mucosal, subcutaneous, intracutaneous, percutaneous or intramuscular immunization.

According to another embodiment of the present invention, the composition is for mucosal immunization.

The mucosal immunization includes oral immunization, intranasal immunization, sublingual immunization, rectal immunization and vaginal immunization, but is not limited thereto.

As verified in the examples below, the vaccine composition increases the production of serum antigen-specific IgA. In addition, it was verified that the vaccine composition increases the production of fecal antigen-specific IgG.

Since the infectious virus vaccine composition of the present invention is similar to the vaccine composition for a neurodegenerative disease in terms of FlaB protein, use as a pharmaceutical composition, and the like, descriptions of content common to the nucleotide and the recombinant protein are omitted in order to avoid excessive complication of the specification.

Advantageous Effects

Features and advantages of the present invention are summarized as follows.

(a) The present invention provides a vaccine composition for a neurodegenerative disease and a vaccine composition for an infectious virus, each of which induces a conformer antigen recognizing antibody.

(b) The vaccine compositions of the present invention induce the production of conformer antigen recognizing antibodies.

(c) Such conformer antigen recognizing antibodies have high specificity to antigens, and thus can be favorably used in the alleviation, prevention, or treatment of diseases.

DETAILED DESCRIPTION

Figure 1:
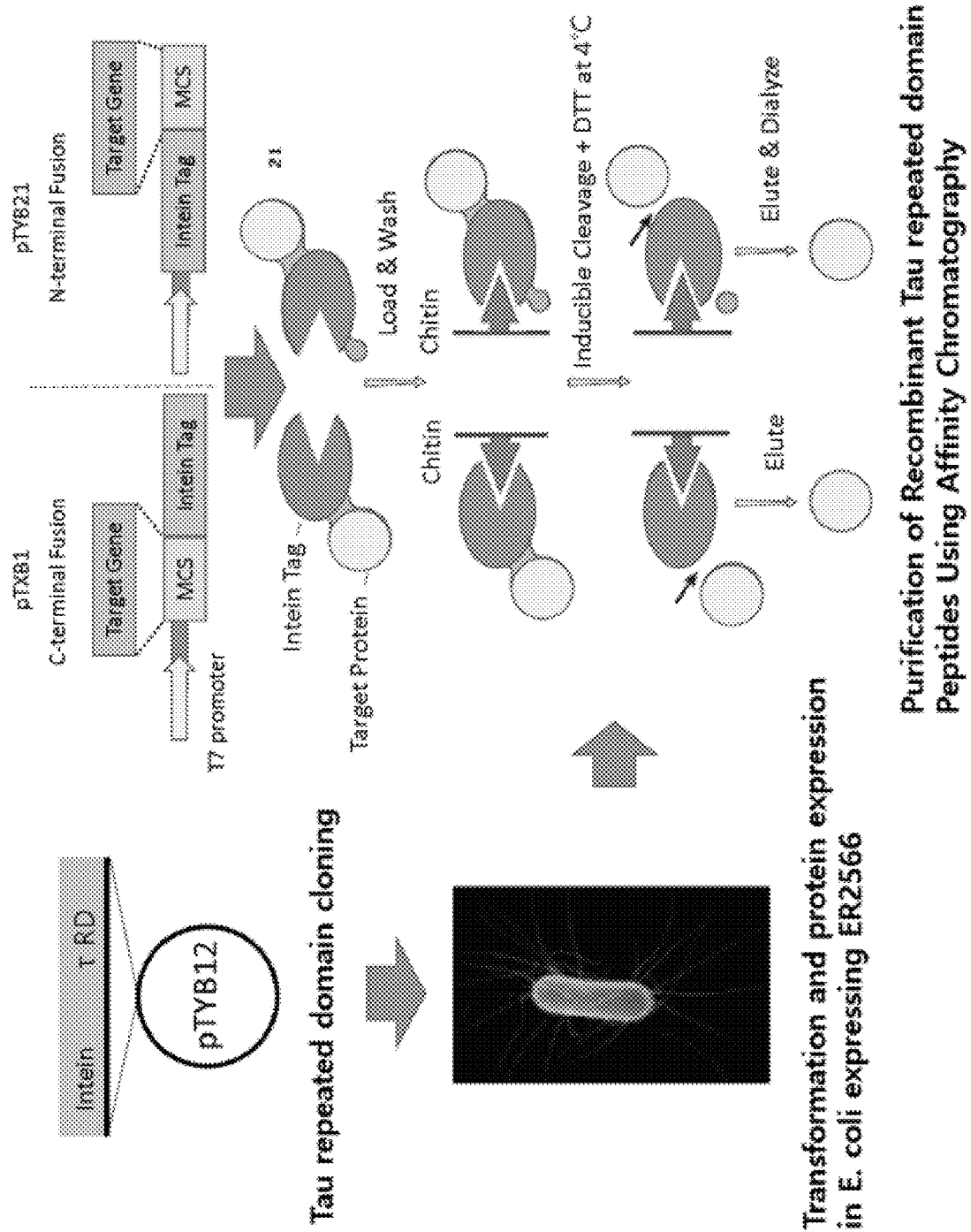
FIG. 1 schematically shows a procedure of cloning a repeated domain (RD) of tau (τ) protein.

Hereinafter, the present invention will be described in detail with reference to examples. These examples are only for illustrating the present invention more specifically, and it will be apparent to those skilled in the art that the scope of the present invention is not limited by these examples.

Example 1: Production of Alzheimer's Disease Immunization Vaccine

Materials

Culture and Storage of Each Strain

The *E. coli* strains used in the present invention were incubated in Luria Bertani (LB) medium (Difco Co.). After the incubation, the strains used were stored in an ultralow-temperature refrigerator after glycerol was added to 30%. The strains and plasmids used in the present invention are summarized in Table 1.

TABLE 1

| Strain or plasmid | Description | Origin |
|---|---|---|
| Strain | | |
| DH5α | F-φ80dlacZM15(lacZYA-argF)U169deoR recA1 endA1 hsdR17(rK-mk+) phoA supE44 λ-thi-gryA96 relA1 | ATCC |
| ER2566 | F-λ-fhuA2[Ion]ompTlacZ::T7 gene1 gal sulA11(mcrC-mrr)114::IS10Rmcr-73::miniTn10-TetS)2R(zgb-210::Tn10)(TetS)endA1[dcm] | New England Biolabs, Inc. |
| Plasmid | | |
| pTYB12 | N-terminal fusion expression vector, intein tag:Apr being fused to N-terminal of target protein | New England Biolabs, Inc. |

Methods and Results

1. Protein Expression and Purification a. Expression and Purification of Flab Recombinant Protein Derived from *Vibrio vulnificus*

FlaB recombinant protein was prepared using the genetic sequence (SEQ ID NO: 1) of Flab, which is a flagellar structural component of *Vibrio vulnificus* CMCP6. In order to obtain a DNA fragment for N-terminal or C-terminal fusion of the flagellin gene flaB, the 1.1 kbp-DNA fragment including flaB gene for N-terminal fusion or C-terminal fusion was amplified using a pair of FlaB-N and FlaB-C primers described in SEQ ID NO: 8 and SEQ ID NO: 9, respectively. That is, PCR reaction using each primer was conducted under conditions of initial denaturation at 95° C. for 5 minutes, 30 cycles of denaturation at 95° C. for 30 seconds, annealing at 60° C. for 30 seconds, and extension at 2° C. for 1 minute, and a final reaction at 2° C. for 10 minutes.

The Intein-CN system by NEB was used as an expression system for the expression of *E. coli*. The pTYB12 plasmid of the corresponding system was treated with restriction enzymes EcoRI and PstI, and then the amplified flaB PCR product was ligated thereto (pCMM11101). The ligated plasmid was transformed in the *E. coli* ER2566 expression strain through electric transformation, and only strains living on LB agar plate containing ampicillin, which is a selective marker of the pTYB12 plasmid, were selected, and it was investigated using the PCR primers of SEQ ID NO: 8 and SEQ ID NO: 9 whether the strains contain the corresponding gene product (CMM11101).

The expression of CMM11101 *E. coli* strain was induced through the addition of 0.5 mM 5-bromoindole-3-chloroisopropyl-D-galactopyranoside (IPTG). The FlaB protein of SEQ ID NO: 2 was obtained from the intein fusion protein using a chitin bead column and 1,4-dithiothreitol (1,4-DTT) according to the instructions of the manufacturer (New England Biolabs Inc.). Endotoxins contained in the isolated protein were removed using AffinityPak™ Detoxi Gel™ endotoxin removing gel (Pierce Inc.).

b. Expression and Purification of Recombinant Tau Repeated Domain

A recombinant protein was prepared from, as an antigen, the whole repeated domain (RD) having high correlation to hyperphosphorylation in the human tau (τ) protein by using *E. coli*. For the preparation of the recombinant protein, the corresponding gene (SEQ ID NO:04) was subjected to codon optimization for *E. coli* and gene synthesis (SEQ ID NO: 5). For easy cloning, EcoRI and XhoI restriction enzyme recognition gene sequences were added to the N-terminal and C-terminal, respectively, during gene synthesis. In order to obtain a DNA fragment for fusion, the 1.1 kbp-DNA fragment including tauRD gene for N-terminal fusion or C-terminal fusion was amplified using a pair of tauRD-N primer (SEQ ID NO: 10) and tauRD-C primer (SEQ ID NO: 11). That is, PCR reaction using each primer was conducted under conditions of initial denaturation at 95° C. for 5 minutes, 30 cycles of denaturation at 95° C. for 30 seconds, annealing at 60° C. for 30 seconds, and extension at 72° C. for 1 minute, and a final reaction at 72° C. for 10 minutes. The Intein-CN system by NEB Inc. was used as an expression system for expression of *E. coli*. The pTYB12 plasmid of the corresponding system was treated with restriction enzymes EcoRI and PstI, and then the amplified tauRD PCR product was ligated thereto (pCMM11102). The ligated plasmid was transformed in the *E. coli* ER2566 expression strain through electric transformation, and only strains living on LB agar plate containing ampicillin, which is a selective marker of the pTYB12 plasmid, were selected, and it was investigated using PCR primers of SEQ ID NO: 10 and SEQ ID NO: 11 whether the strains contain the corresponding gene product (CMM11102).

The expression of CMM11102 *E. coli* strain was induced by addition of 0.5 mM 5-bromo-4-indole-3-chloro-isopropyl-D-galactopyranoside (IPTG). The TauRD protein having the amino acid sequence of SEQ ID NO: 3 was obtained from the intein fusion protein by using a chitin bead column and 1,4-dithiothreitol (1,4-DTT) according to the instructions of the manufacturer (New England Biolabs Inc.) Endotoxins contained in the isolated protein were removed using AffinityPak™ Detoxi Gel™ endotoxin removing gel (Pierece Inc.).

Figure 2:
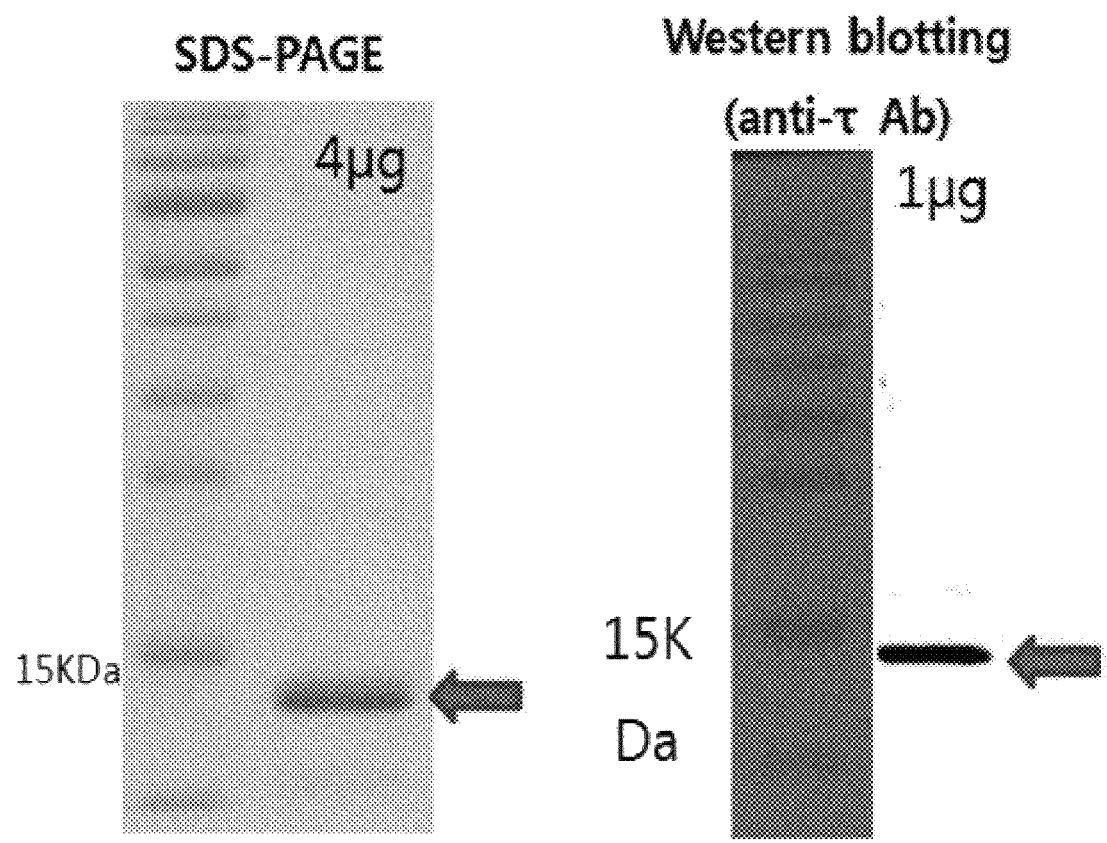
FIG. 2 shows results confirming the cloning of RD of the tau protein. The left panel shows results confirming the expression of RD through SDS-PAGE and the right panel shows results confirming the expression of RD through western blotting. RD indicates a size of 13 kDa.

For the investigation of the expression of the purified recombinant fusion protein, the molecular weight of the recombinant fusion protein was checked using SDS-PAGE, and as a result, it was verified that a 13 kDa-sized recombinant fusion protein was prepared (FIG. 2).

For the investigation of whether the purified recombinant fusion protein was an accurate tau protein, western blotting was conducted using an anti-tau antibody, and as a result, a band specific to the anti-tau protein was confirmed (FIG. 2).

c. Cloning of Gene for Preparing Recombinant FlaB-TauRD Fusion Protein

The flaB gene of pCMM11101 was treated with EcoRI and PstI restriction enzymes and pCMM11102 was also treated with the same enzymes, and then the flaB gene fragment and the pCMM11102 plasmid were purified through agarose gel electrophoresis. These two genes were ligated to prepare pTYB12::flaB-tauRD gene fusion plasmid (pCMM11103). The ligated plasmid was transformed in the *E. coli* ER2566 expression strain through electric transformation, and only strains living on LB agar plate containing ampicillin, which is a selective marker of the pTYB12 plasmid, were selected, and it was investigated using the PCR primers of SEQ ID NO: 8 and SEQ ID NO: 11 whether the strains contain the corresponding gene product (CMM11104).

The expression of CMM11103 *E. coli* strain was induced by addition of 0.5 mM 5-bromoindole-3-chloroisopropyl-D-galactopyranoside (IPTG). FlaB-TauRD fusion protein of SEQ ID NO: 6 was obtained from the intein fusion protein by using a chitin bead column and 1,4-dithiothreitol (1,4-DTT) according to the instructions of the manufacturer (New England Biolabs Inc.) Endotoxins contained in the isolated protein were removed using AffinityPak™ Detoxi Gel™ endotoxin removing gel (Pierece Inc.).

Figure 3:
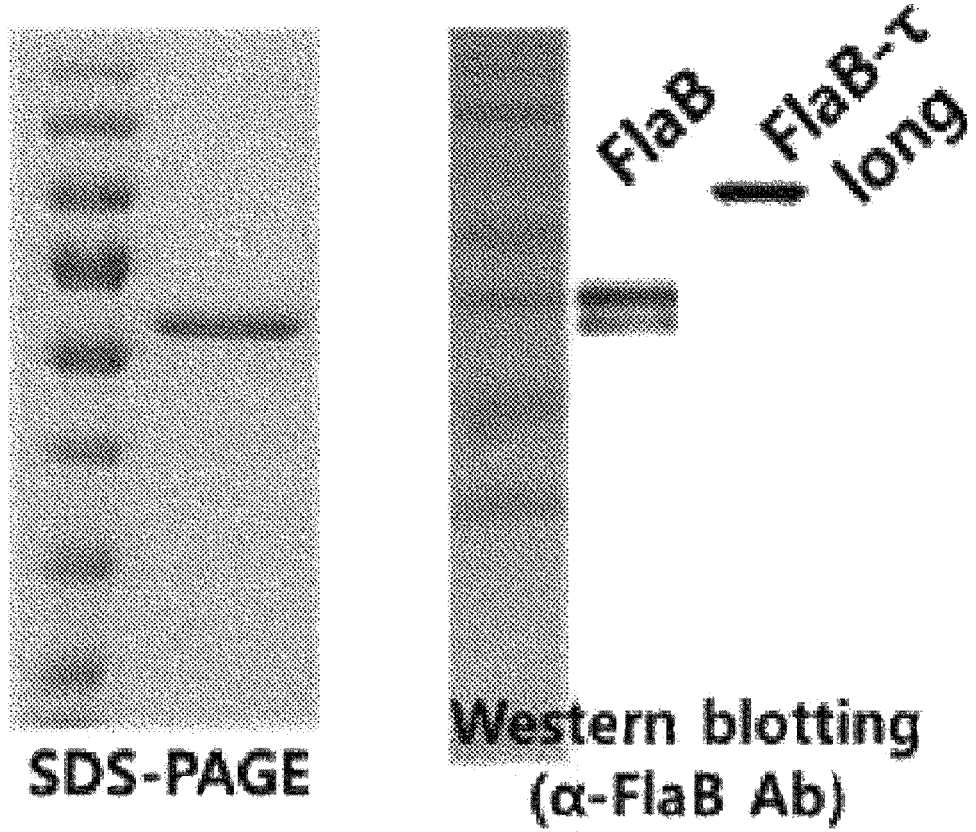
FIG. 3 shows results confirming the cloning of FlaB-TauRD recombinant protein.

For the confirmation of exactness of the purified FlaB-TauRD, SDS-PAGE and western blotting using a FlaB-specific mouse anti-serum were conducted. As a result, it was verified that the purified FlaB-TauRD fusion protein showed a 57 kDa-sized band having an original size thereof, and bound to the Flab-specific anti-serum on the western blot (FIG. 3).

Figure 4:
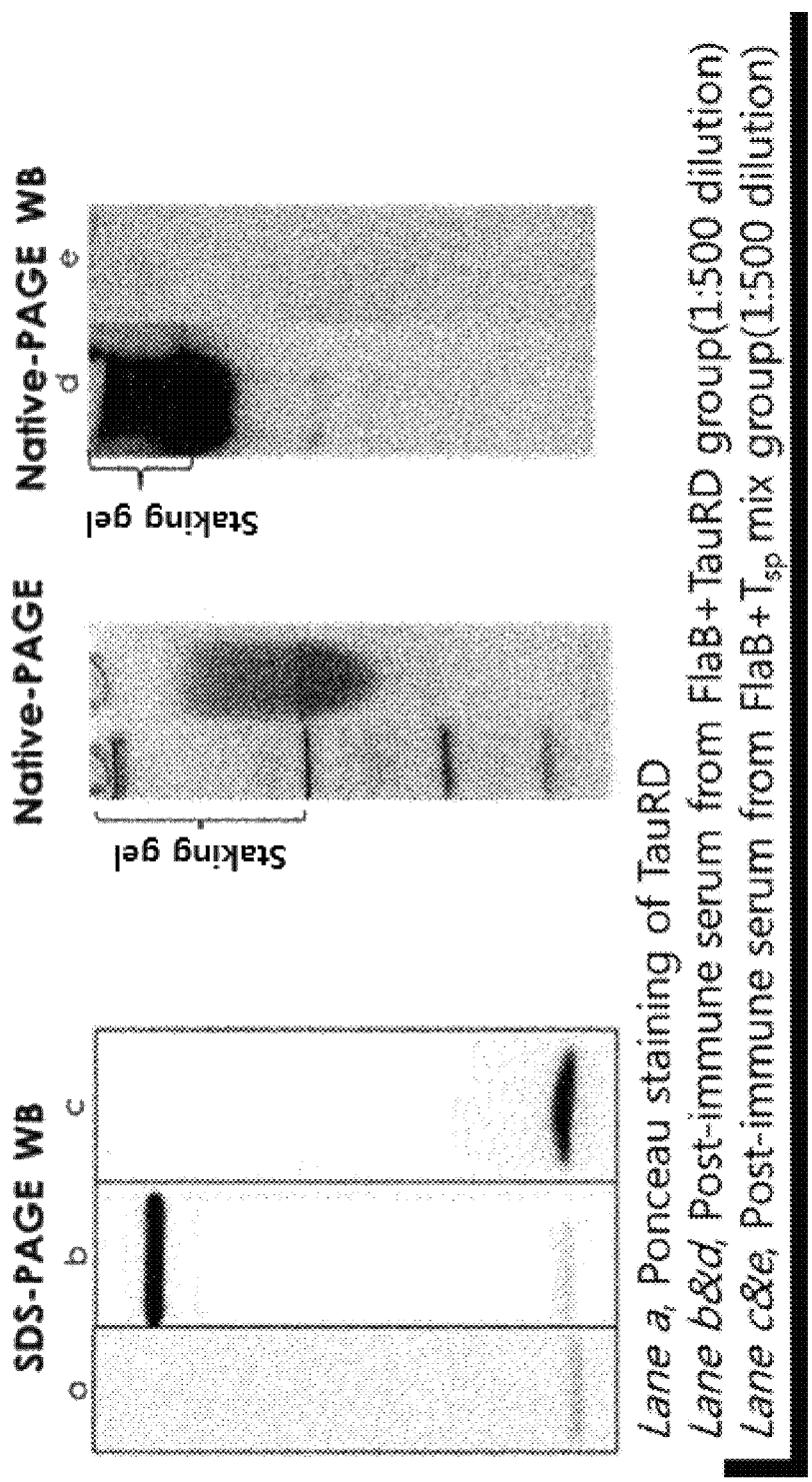
FIG. 4 shows results confirming the production of a conformer structure recognizing antibody by administration of FlaB-TauRD recombinant protein. Experimental results show that an anti-serum obtained by the immunization of FlaB and Tau-Ag, which is obtained from the expression of a portion of Tau protein, induced the production of a "structure recognizing antibody" responding to a paired helical filament (PHF), which is a Tau pathologic conformer.

FIG. 4 shows experimental results that an anti-serum obtained by the immunization of FlaB and Tau-Ag, which is obtained from the expression of a portion of Tau protein, induced the production of a "structure recognizing antibody" responding to a PHF, which is a Tau pathologic conformer. The Tau-Ag used in the immunization was isolated by SDS-PAGE, and then transferred onto a nylon membrane and stained with Ponceau S, and as a result, a monomer protein was confirmed. When a prepared membrane was immuno-blotted with an antibody obtained by the immunization of FlaB and Tau-Ag in the same manner, a monomer band was almost not recognized, and a very small amount of multimer structures, which had not been observed in Ponceau S staining, were strongly recognized. In order to prove this, immunoblotting was conducted after native PAGE while multimeric structures were maintained, and as a result, it was verified that the immune serum strongly responded to the multimeric structures, which have not been recognized by standard serum. This indicates that the anti-serum induced by the present invention shows significantly high binding strength to tau aggregates causing Alzheimer's disease.

d. Characterization of Recombinant FlaB-TauRD Protein

① Investigation of TLR5 Stimulating Ability of Recombinant FlaB-TauRD Protein

Figure 5:
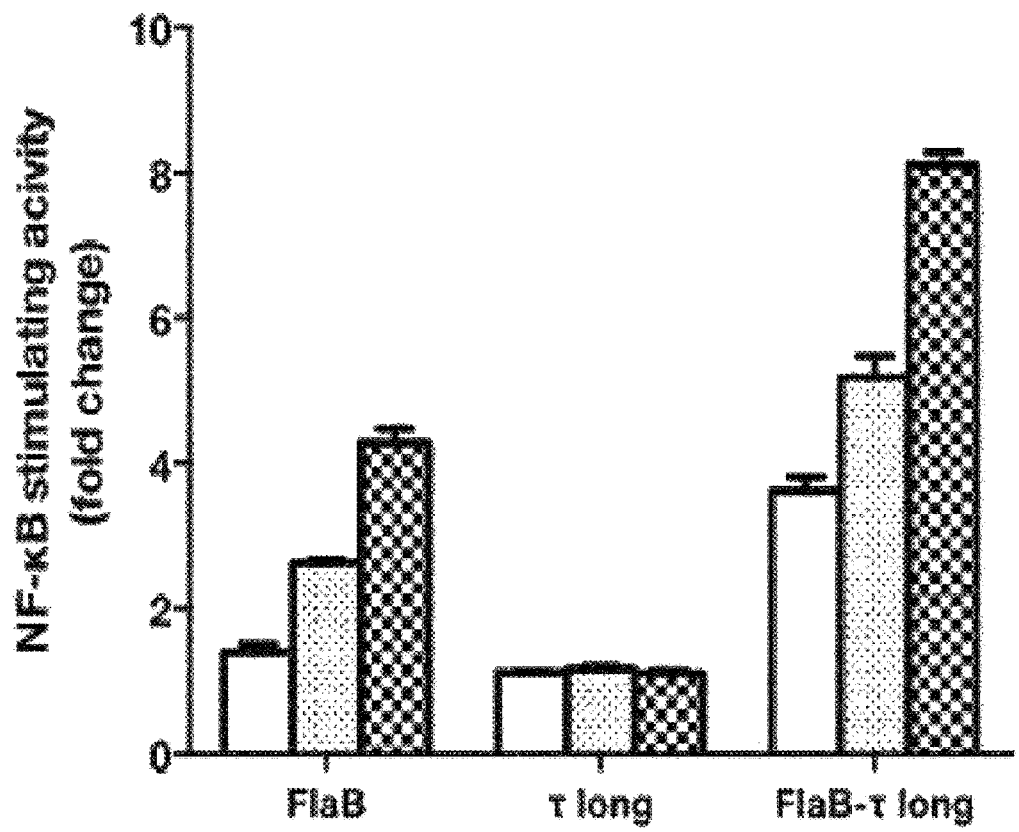
FIG. 5 shows results confirming stimulation activity of FlaB, TauRD, and FlaB-TauRD to tall-like receptor 5 (TLR5).

For the investigation of whether the purified recombinant tau-RD peptide itself retains stimulation ability to TLR5 as an action point of flagellin, 293-T cells were dispensed at $1 \times 10^5$ cells per well in a well-plate incubator, and incubated overnight. Then, NF-κ-Luc plasmid (obtained from Prof. Kim Jong-Mok of the Department of Microbiology, Hanyang University), TLR5 gene-cloned P3×Flag-hTLR-5 plasmid (obtained from Steven B. Mizel of the Department of Microbiology and Immunology, Wake Forest University School of Medicine, USA), and β-galactosidase expression control plasmid (Clontech) were simultaneously introduced into the cells by using Effectene (QIAGEN). After additional incubation for 24 hours, the medium was exchanged with a fresh medium. The FlaB and the tau-RD peptide isolated by IMPACT system were treated for a predetermined time, and luciferase activity was measured using a luminescence analyzer (Luminometer, Berthold Inc.) to check the degree of transcription of NF-κB. The results are shown in FIG. 5. In the results of FIG. 5, the recombinant tau-RD peptide used as an antigen did not show TLR5 stimulating ability, but the FlaB-TauRD fusion protein showed significant TLR5 stimulating ability compared with FlaB.

Figure 6:
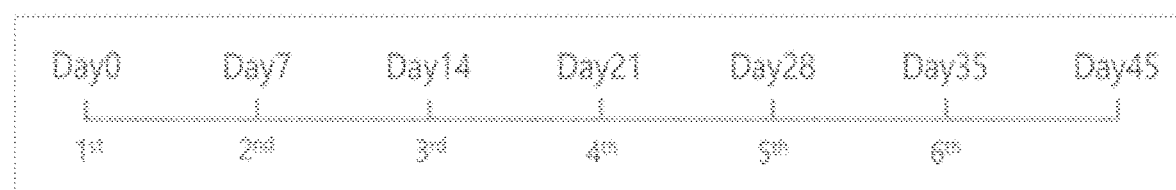
FIG. 6 shows an immunization schedule of FlaB-TauRD recombinant protein.

① Comparison of Tau Antigen-Specific Antibody Forming Ability According to Administration of Recombinant FlaB-TauRD Mix Vaccine After six-week-old female Balb/c mice (Orient Bio, Korea) were intranasally immunized with the flagellin tau-RD peptide mix vaccine of the present invention three times, five times, and six times at weekly intervals, serum for each case was obtained to compare the formation of the tau-RD peptide-specific antibody (FIG. 6). For comparison, the anti-serum obtained by coating the recombinant flagellin tau-RD protein on the 96-well plate ELISA plate and conducting immunization was serially diluted two-fold, and checked through indirect ELISA method.

Figure 7A:
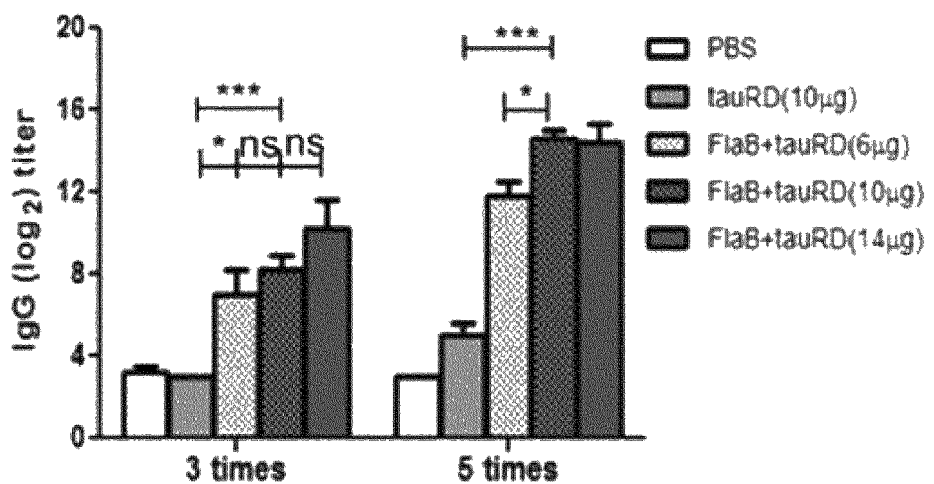
FIGS. 7a and 7b show IgG production ability of vaccines containing TauRD and FlaB-TauRD recombinant protein according to the number of times of vaccine immunization and the concentration of vaccine.

As a result, the flagellin tau-RD peptide mix vaccine showed high serum IgG formation compared with the tau-RD peptide alone immunization group. As for the treatment with antigen at different doses, there was not a statistically significant dose-response relationship in three times immunization, but a statistically significant difference in antigen-specific antibody forming ability was confirmed between the antigen 6 μg treatment group and the antigen 10 μg treatment group in five times immunization. A statistically significant difference in antigen-specific antibody forming ability was not confirmed between the 10 μg treatment group and the 14 μg treatment group (FIG. 7*a*).

Figure 7B:
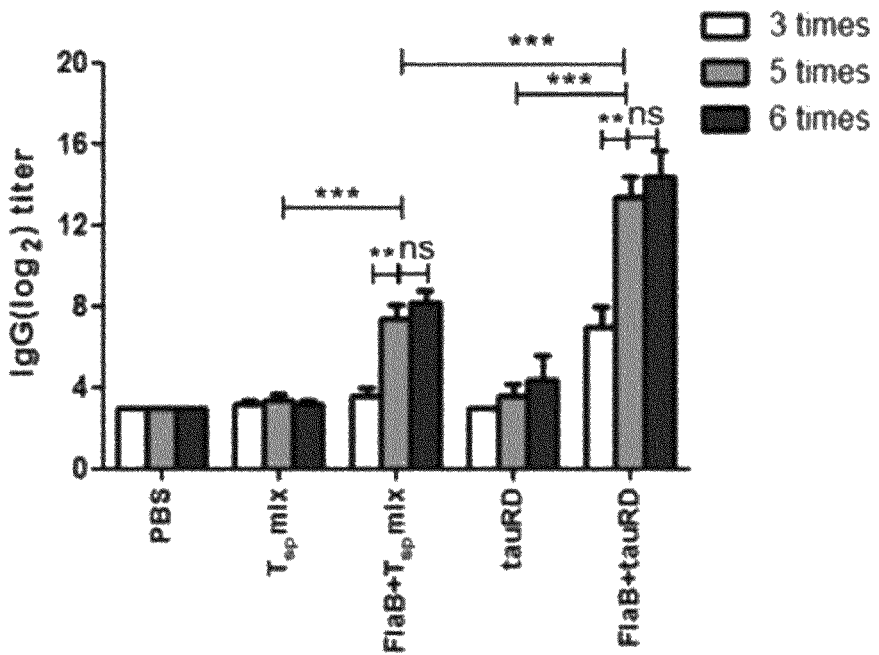
Figure 8:
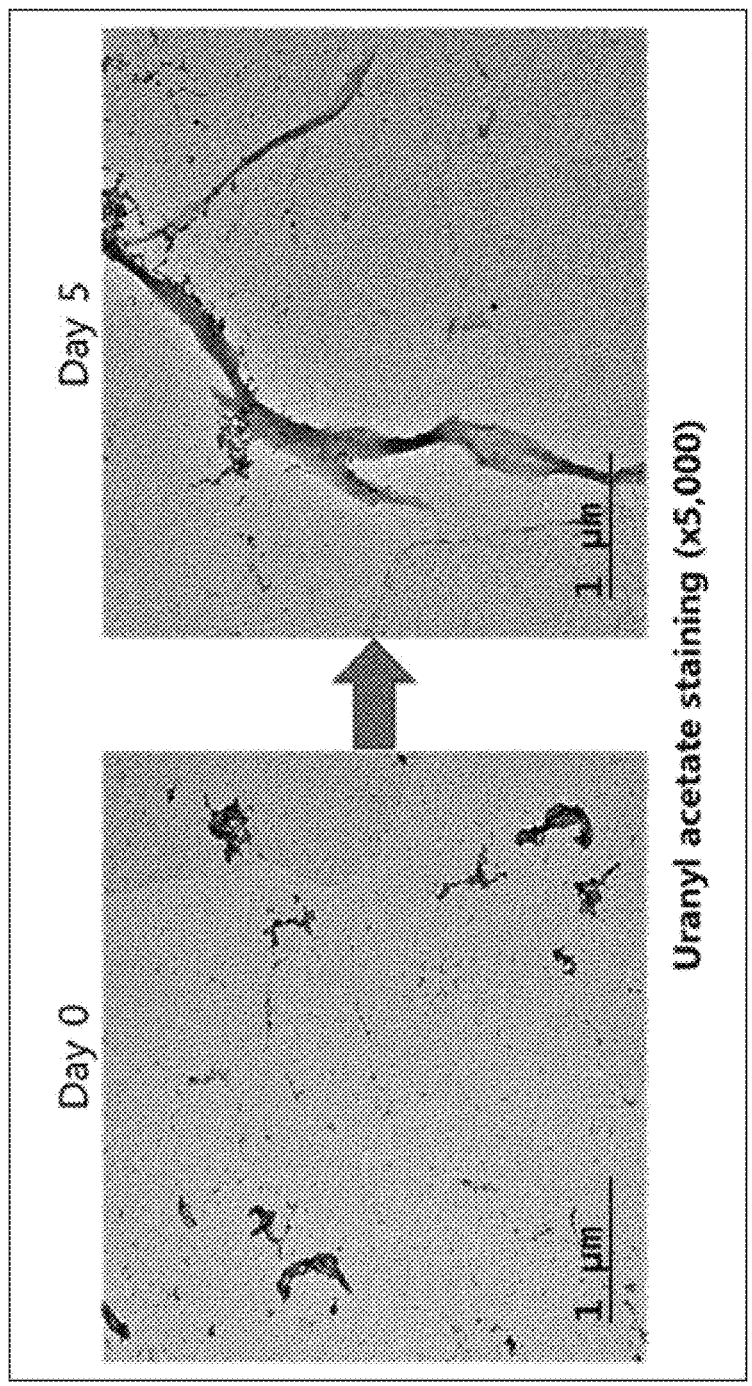
FIG. 8 shows images depicting that FlaB-TauRD recombinant protein formed aggregates in the form of PHFs.

In the comparison results of antigen-specific antibody forming ability after three times, five times, and six times immunization, statistically significant differences in antigen-specific antibody forming ability could be confirmed between the three-time administration groups and the five-time administration groups, but statistically significant differences in antigen-specific antibody forming ability could not be confirmed between the five-time administration groups and the six-time administration groups (FIG. 7*b*).

③ Formation of Recombinant FlaB-TauRD Protein Aggregates

It was confirmed through an electron microscope that the anti-serum induced by the present invention, a specific antigen in the brain, self-formed aggregates, and after 5 days of purification, formed aggregates in the form of PHFs.

④ Induction of Recombinant FlaB-TauRD Protein Aggregates

The tau protein aggregates (aggregates being induced by treatment of purified tau-RD peptide with heparin) was stained with tioflavin S (green), which specifically binds to a β-sheet structure of a protein, and an anti-serum obtained by immunization of a product by the present invention was stained with Alexa fluor 633 (Molecular probe) labeled anti-mouse IgG rabbit IgG, and then the comparison on the presence or absence of the binding between the tau protein and the anti-serum and the degree of the binding was conducted by using a confocal laser microscope.

Figure 9:
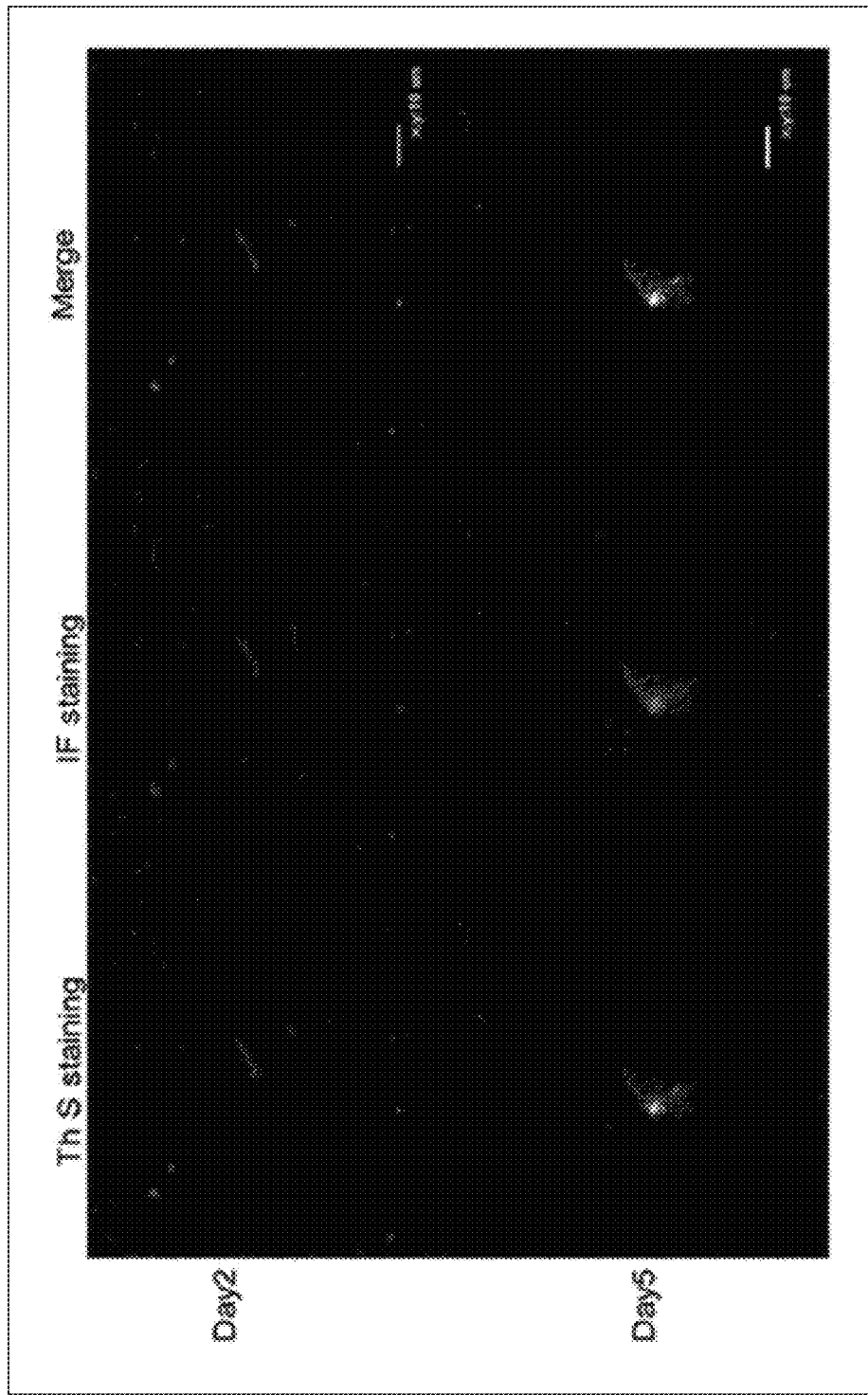
FIG. 9 shows results confirming the production of a structure recognizing antibody by administration of FlaB-TauRD recombinant protein. The results confirm that an antibody produced by simultaneous reaction of thioflavin S (Th-S), which selectively binds to the beta sheet, and an anti-serum was colocalized while PFH molecules formed a neurofibrillary tangle-like structure.

As a result of the experiment, the anti-serum induced by the present invention showed a binding aspect to the tau protein on the fifth day of aggregation induction (more aggregated) than on the second day of aggregation induction (FIG. 9).

⑤ Aggregation Inhibiting Effect of Recombinant FlaB-TauRD Protein

For the investigation of a tau aggregation inhibiting effect of the anti-tau serum induced by the present invention, the recombinant tau-RD peptide was treated with the anti-serum induced by the present invention, followed by anti-serum removal, and then the aggregation of a tau peptide was induced by using heparin, and the degree of aggregate formation was checked through a transmission electron microscope.

Figure 10:
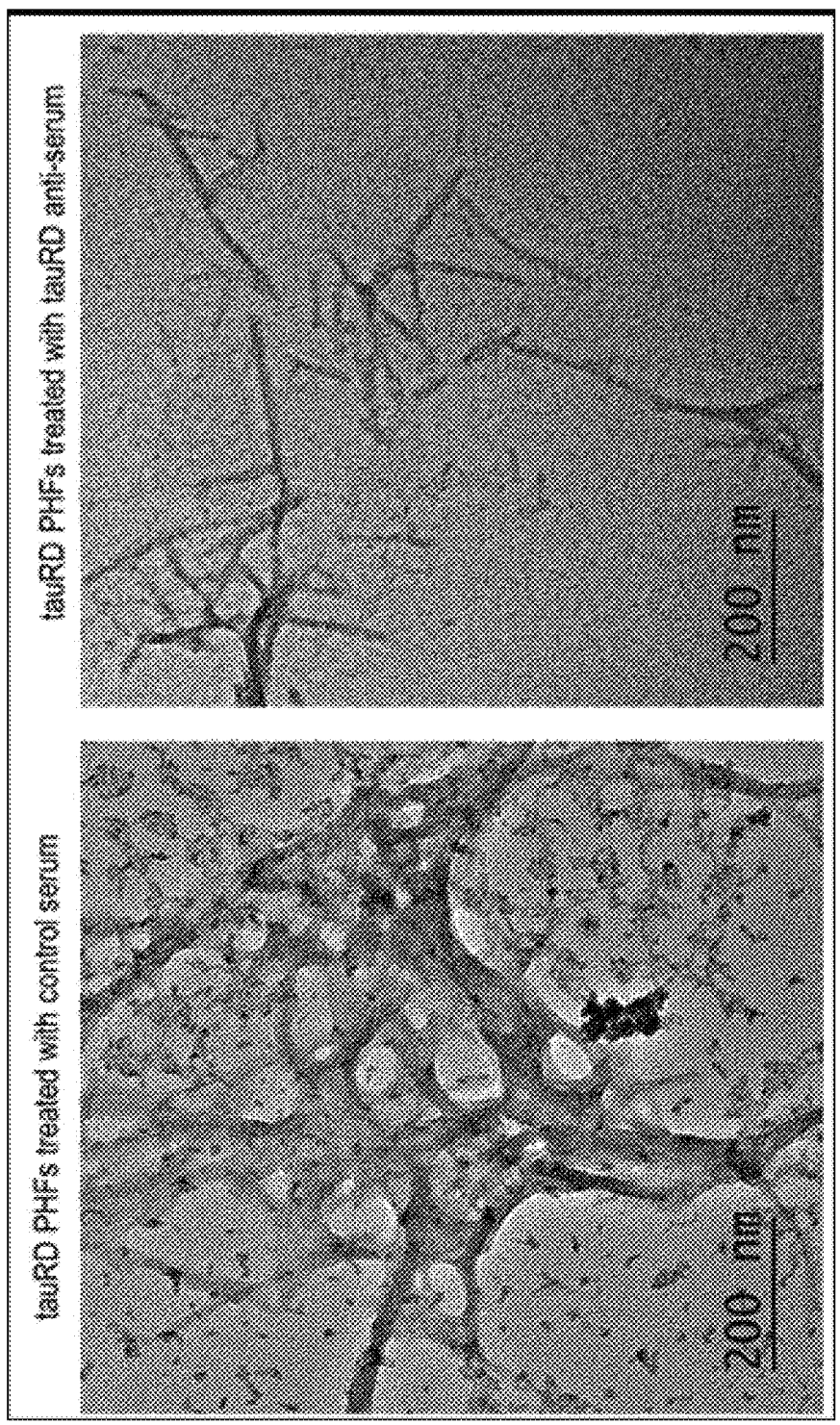
FIG. 10 shows a tau protein aggregation inhibiting effect by an anti-serum to FlaB-TauRD recombinant protein.

The aggregation of tau protein was observed when the tau protein was pre-treated with control serum obtained by immunization of saline, but the aggregation of the tau protein was observed to deteriorate when the tau protein was pre-treated with the anti-serum induced by the present invention (FIG. 10).

⑥ Phagocytic Activity of Recombinant FlaB-TauRD Protein

An experiment was conducted to investigate whether the anti-serum induced by the present invention promotes tau aggregate opsonic phagocytosis of microglial cell line (BV2 cell line, dispensed by Professor Moon, Chang-Jong of Chonnam National University Medical School), which are specific antigen-presenting cells in the brain). The aggregation of the recombinant tau-RD peptide was induced for three days by using heparin, followed by staining with FNR 488 (Green, Bioacts, Korea). Tau aggregates were broken by sonication for 10 seconds, and then the incubated BV2 cell line was treated with the tau aggregates together with the anti-tau serum by the present invention. Control serum obtained through PBS immunization was used as a control. After incubation for 30 minutes, the nuclei of BV2 cells were stained with DAPI (blue) and the cell membranes of BV2 cells were stained with wheat germ agglutinin (WGA, red), and then a comparison about the presence or absence of phagocytosis of the broken tau aggregates and the degree of phagocytosis was conducted using a confocal microscope.

Figure 11:
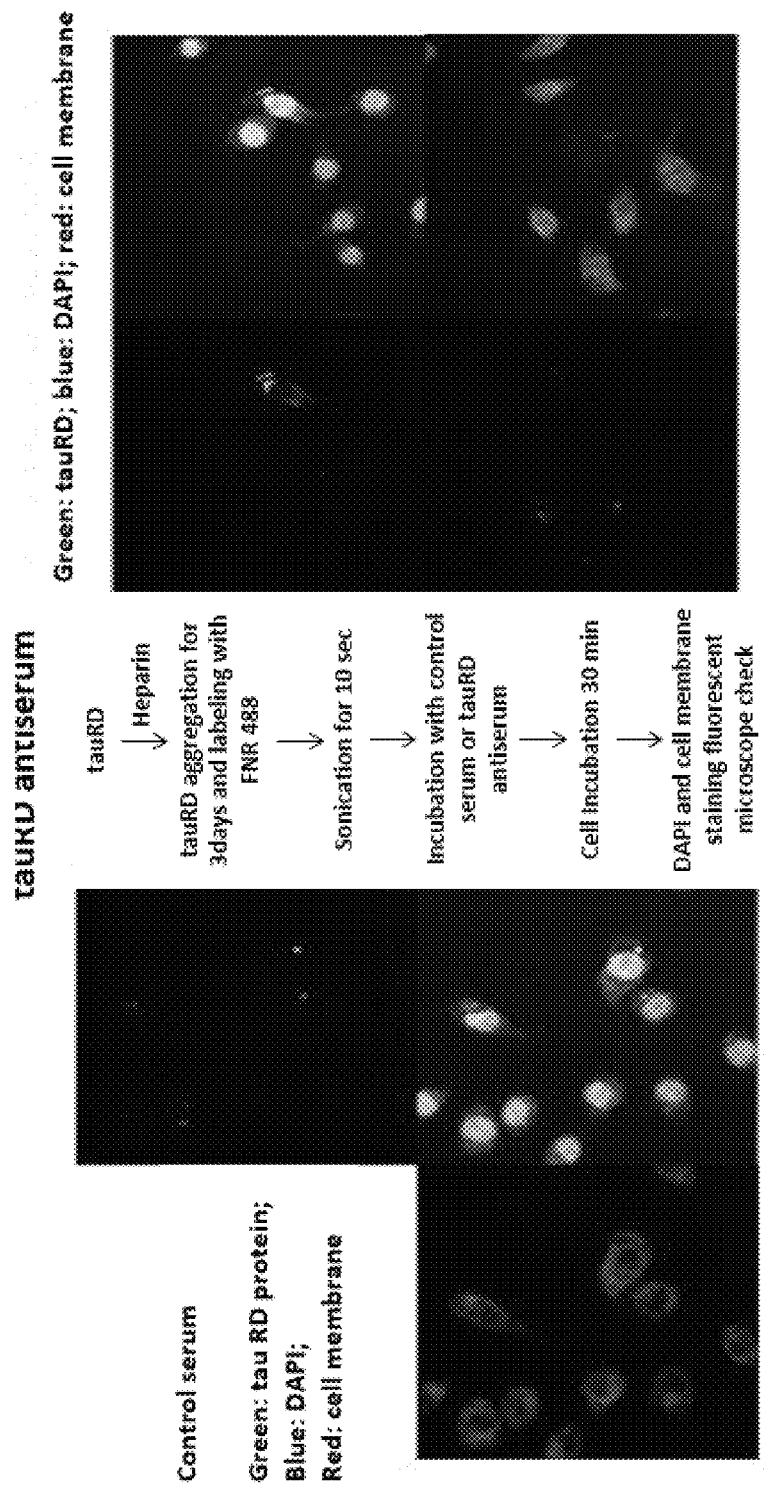
FIG. 11 shows an opsonic phagocytosis stimulating effect of an anti-serum to FlaB-TauRD recombinant protein.

As a result, the broken tau aggregates treated with the anti-serum induced by the present invention were phagocytized by BV2 cells, but such a phenomenon was not found in the control serum treatment group. This indicates that the anti-serum induced by the present invention provides high opsonic phagocytosis ability to the specific antigen presenting cells of the brain (FIG. 11).

Example 2: Preparation of Norovirus Immune Vaccine a. Norovirus P Domain Antigen Sequence and Codon Optimization Thereof For DNA for an antigen for the preparation of a norovirus vaccine, norovirus P domain-cloned pGEX-4T-1::VAxxx obtained from Cho Kyung-Oh, a professor of Chonnam National University was used. The inserted gene sequence was as described in SEQ ID NO: 12.

b. Cloning of Gene for Preparing Recombinant Pd Antigen

In order to obtain a DNA fragment for fusion of N-terminal or C-terminal of the Pd gene for an antigen, the 1.1 kbp-DNA fragment including Pd gene was amplified by using a pair of Pd—N and Pd—C primers described in SEQ ID NO: 16 and SEQ ID NO: 17 and, as a template, the Pd-containing plasmid of SEQ ID NO: 12. That is, PCR reaction using each primer was conducted under the conditions of initial denaturation at 95° C. for 5 minutes, 30 cycles of denaturation at 95° C. for 30 seconds, annealing at 60° C. for 30 seconds, and extension at 72° C. for 1 minute, and a final reaction at 72° C. for 10 minutes.

The IMPACT-CN system by NEB Inc. was used as an expression system for expression of *E. coli*. The pTYB12 plasmid of the corresponding system was treated with restriction enzymes EcoRI and PstI, and then the amplified Pd PCR product was ligated thereto (pCMM11105). The ligated plasmid was transformed in the *E. coli* ER2566 expression strain through electric transformation, and only strains living on LB agar plate containing ampicillin, which is a selective marker of the pTYB12 plasmid, were selected, and it was investigated using PCR primers of SEQ ID NO: 16 and SEQ ID NO: 17 whether the strains contain the corresponding gene product (pCMM11105).

The expression of CMM11105 *E. coli* strain was induced by addition of 0.5 mM 5-bromoindole-3-chloroisopropyl-D-galactopyranoside (IPTG). The FlaB-Pd fusion protein of SEQ ID NO: 15 was obtained from the intein fusion protein by using a chitin bead column and 1,4-dithiothreitol (1,4-DTT) according to the instructions of the manufacturer (New England Biolabs Inc.) Endotoxins contained in the isolated protein were removed using AffinityPak™ Detoxi Gel™ endotoxin removing gel (Pierece Inc.).

Figure 12:
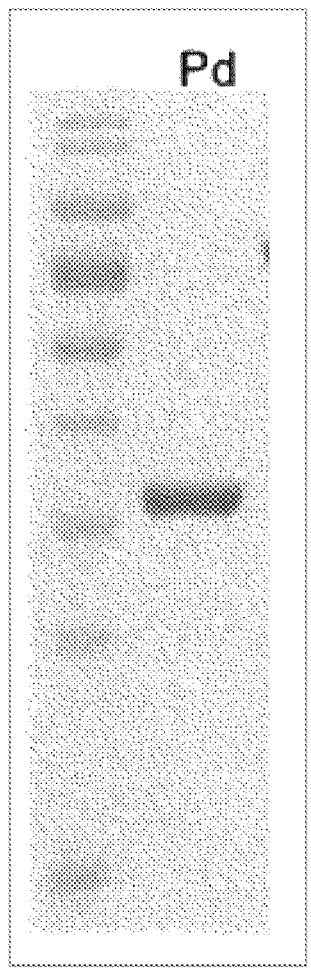
FIG. 12 shows results of expression and purification of norovirus P domain.

For the investigation of exactness of the purified recombinant Pd protein, SDS-PAGE was conducted (FIG. 12). As a result, the purified recombinant Pd protein showed a 44 kDa-sized band having an original size thereof.

c. Cloning of Gene for Preparing Recombinant Flag Pd Fusion Protein

The flaB gene of pCMM11101 was treated with EcoRI and PstI restriction enzymes and pCMM11105 was also treated with the same enzymes, and then the flaB gene fragment and the pCMM11105 plasmid were purified through agarose gel electrophoresis. These two genes were ligated to prepare pTYB12::flaB-Pd gene fusion plasmid (pCMM11106). The ligated plasmid was transformed in the *E. coli* ER2566 expression strain through electric transformation, and only strain living on LB agar plate containing ampicillin, which is a selective marker of the pTYB12 plasmid, were selected, and it was investigated using PCR primers of SEQ ID NO: 8 and SEQ ID NO: 17 whether the strains contain the corresponding gene product (CMM11106).

The expression of CMM11105 *E. coli* strain was induced by addition of 0.5 mM 5-bromoindole-3-chloroisopropyl-D-galactopyranoside (IPTG). The FlaB-Pd protein of SEQ ID NO: 15 was obtained from the intein fusion protein by using a chitin bead column and 1,4-dithiothreitol (1,4-DTT) according to the instructions of the manufacturer (New England Biolabs Inc.) Endotoxins contained in the isolated protein were removed using AffinityPak™ Detoxi Gel™ endotoxin removing gel (Pierece Inc.).

Figure 13:
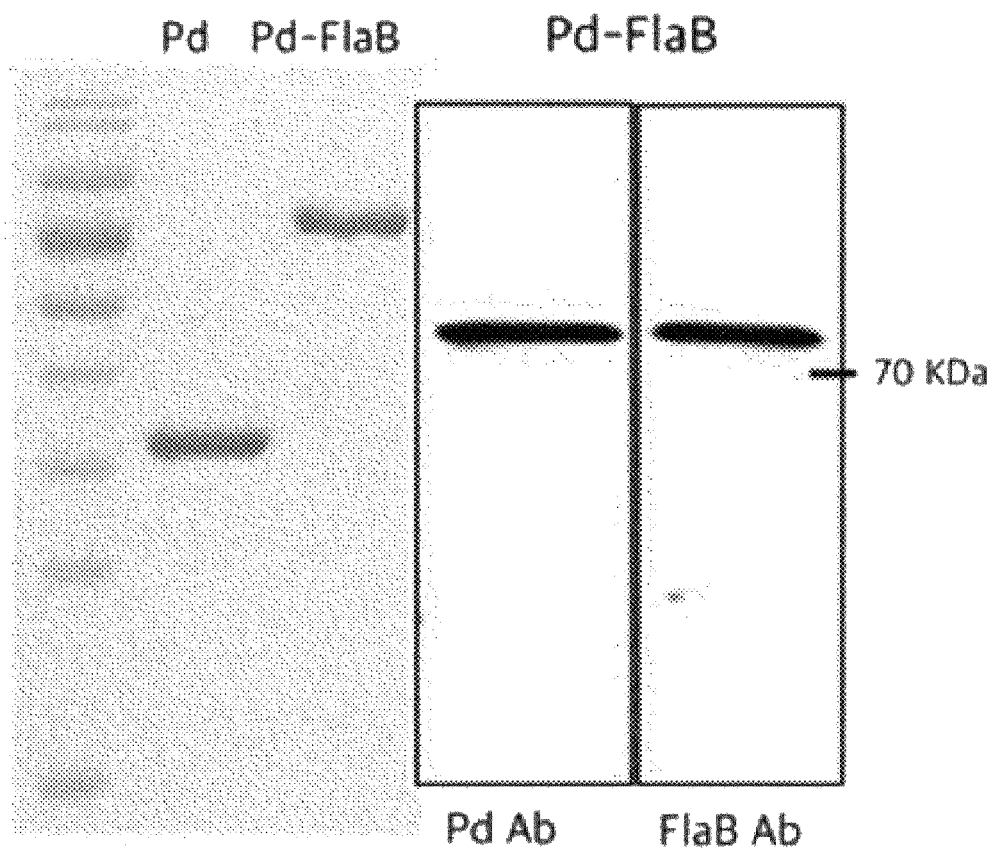
FIG. 13 shows expression and purification of Pd-FlaB recombinant protein and specific binding of Pd-FlaB recombinant protein to Pd anti-serum and Flab anti-serum.

For the confirmation of exactness of the purified FlaB-Pd, SDS-PAGE and western blotting using a FlaB- or Pd-specific mouse anti-serum were conducted. As a result, it was verified that the purified FlaB-Pd fusion protein showed a 44 kDa-sized band having an original size thereof, and bound to the Flab- and Pd-specific anti-serum on the western blot (FIG. 13).

d. Characterization of Recombinant FlaB-Pd Protein

① TLR5 Stimulating Ability of Recombinant FlaB-Pd Protein

Figure 14:
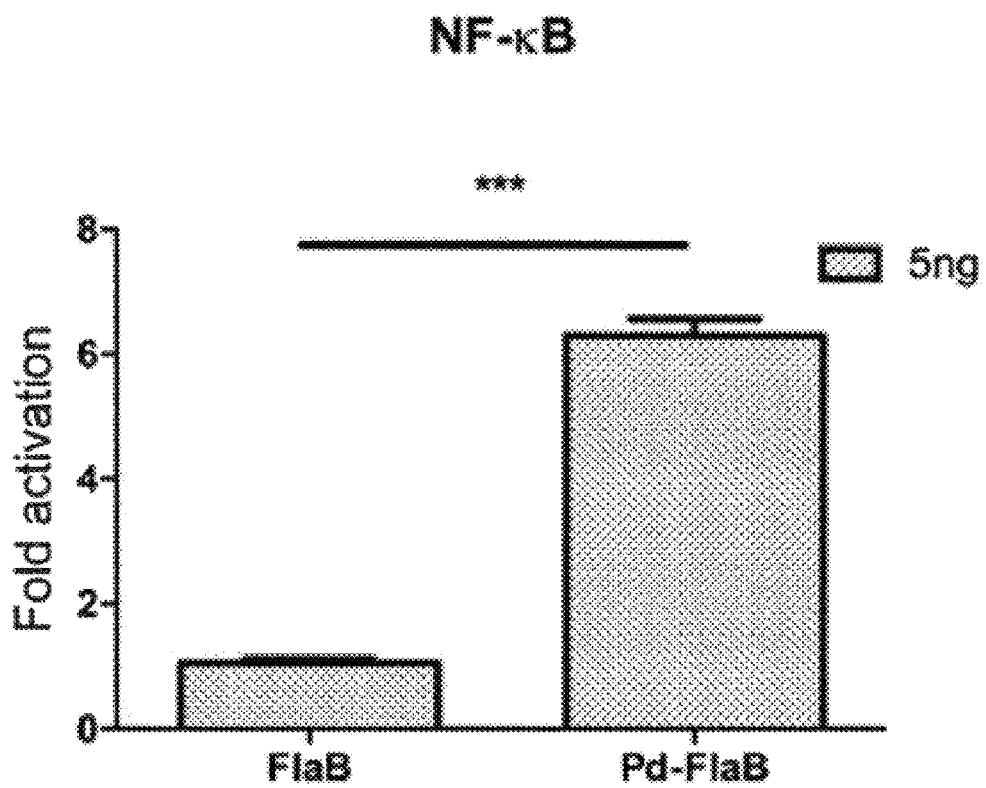
FIG. 14 shows results confirming stimulation activity of FlaB and Pd-FlaB to tall-like receptor 5 (TLR5).
Figure 15:
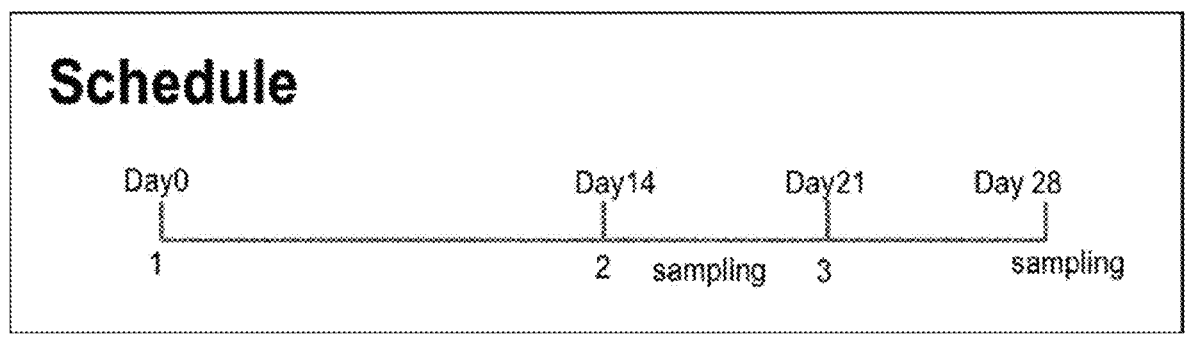
FIG. 15 shows an immunization schedule of Pd-FlaB recombinant protein.
Figure 16:
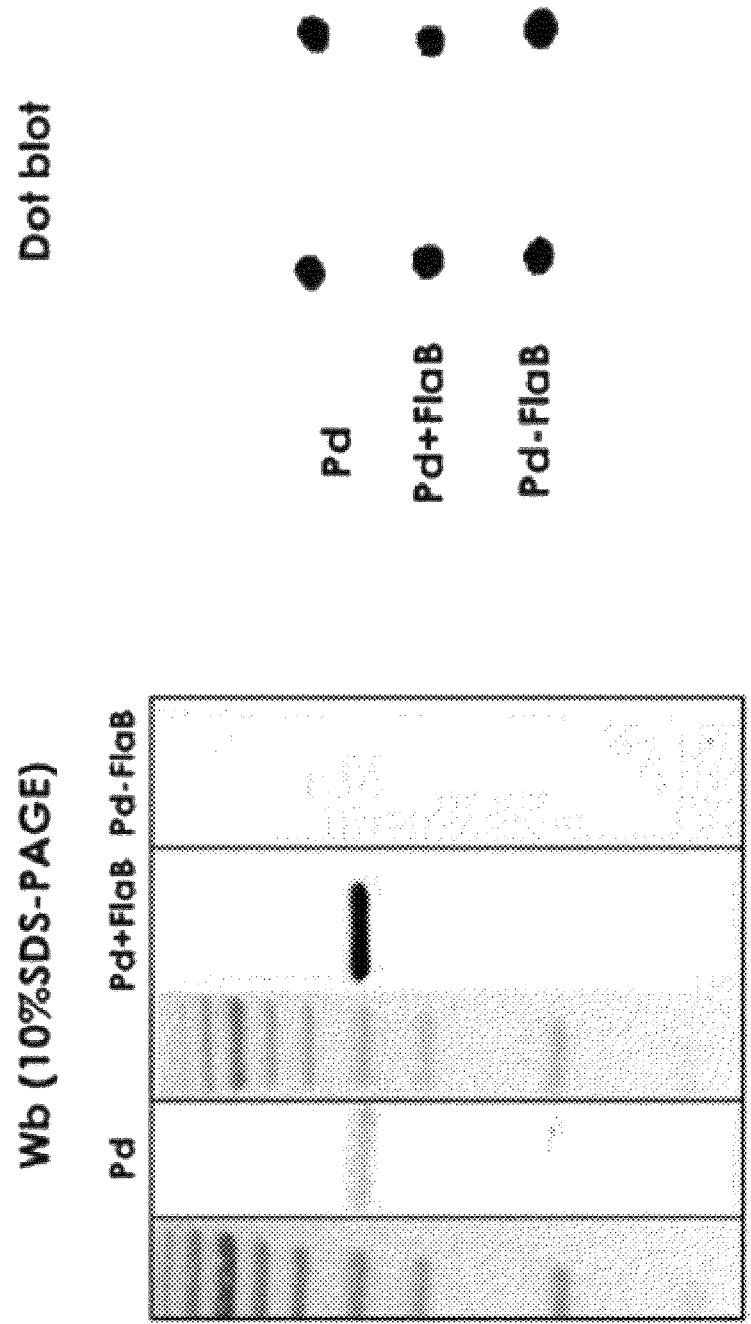
FIG. 16 shows results of the introduction of structure recognizing antibody production through protein engineering. Unlike a tau antigen, a structure recognizing antibody was not produced merely when the norovirus Pd antigen was administered in mixing with flagellin (left panel), but a structure recognizing antibody, which did not recognize a monomer only when immunization was conducted using Pd-flagellin fusion antigen and responded to an antigen only on a dot blot experiment using a cell lysate with an antigen structure maintained, was produced (right panel).
Figure 17:
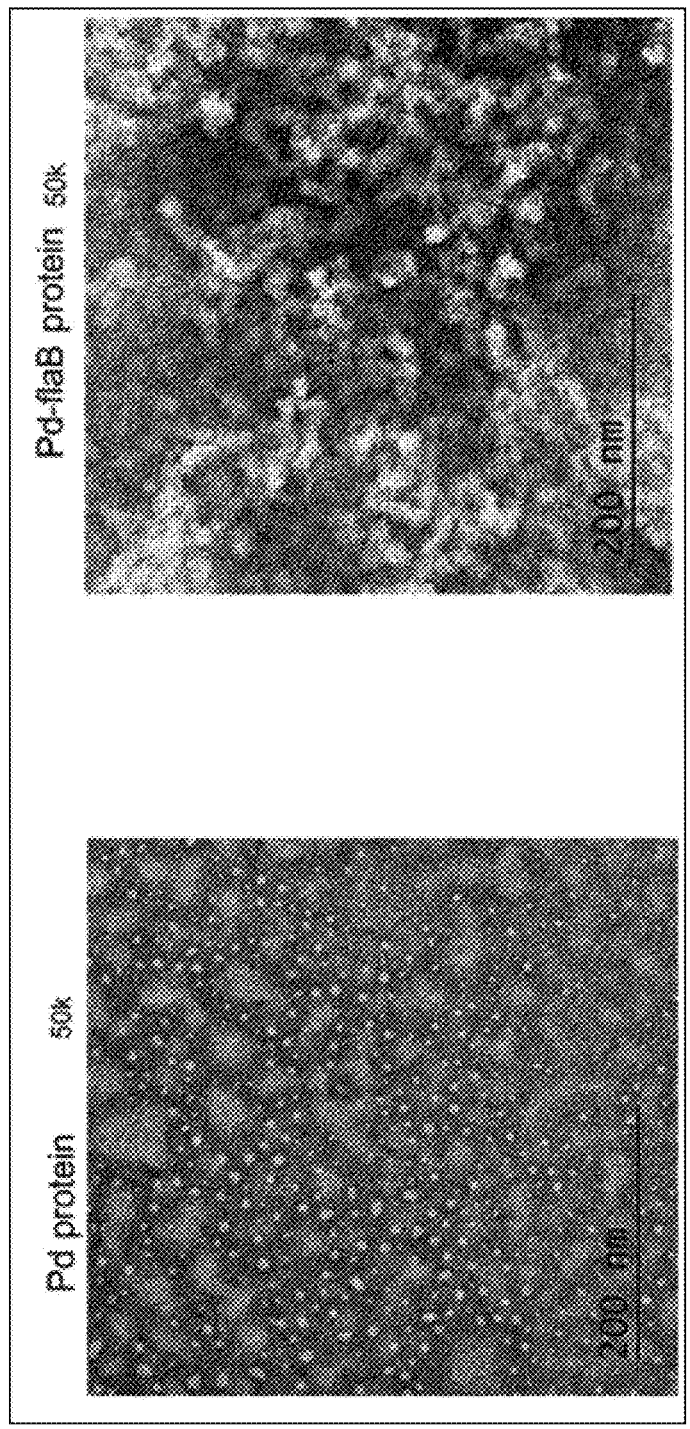
FIG. 17 shows an electron microscope observation image of Pd-FlaB recombinant protein.

For the investigation of biological activity of FlaB-Pd fusion protein, 293-T cells were dispensed at $1\times10^5$ cells per well in a 24-well plate incubator, and incubated overnight. Then, NF-κ-Luc plasmid (obtained from Prof. Kim Jong-Mok of the Department of Microbiology, Hanyang University), TLR5 gene-cloned P3×Flag-hTLR-5 plasmid (obtained from Steven B. Mizel of the Department of Microbiology and Immunology, Wake Forest University School of Medicine, USA), and β-galactosidase expression control plasmid (Clontech) were simultaneously introduced into the cells by using Effectene (QIAGEN). After additional incubation for 24 hours, the medium was exchanged with a fresh medium. The FlaB-Pd fusion protein isolated by the IMPACT system was treated for a predetermined time, and luciferase activity was measured using a luminescence analyzer (Luminometer, Berthold Inc.) to check the degree of transcription of NF-κB. The results are shown in FIG. 14.

② Recognition of Recombinant FlaB-Pd Protein Structure

Figure 18:
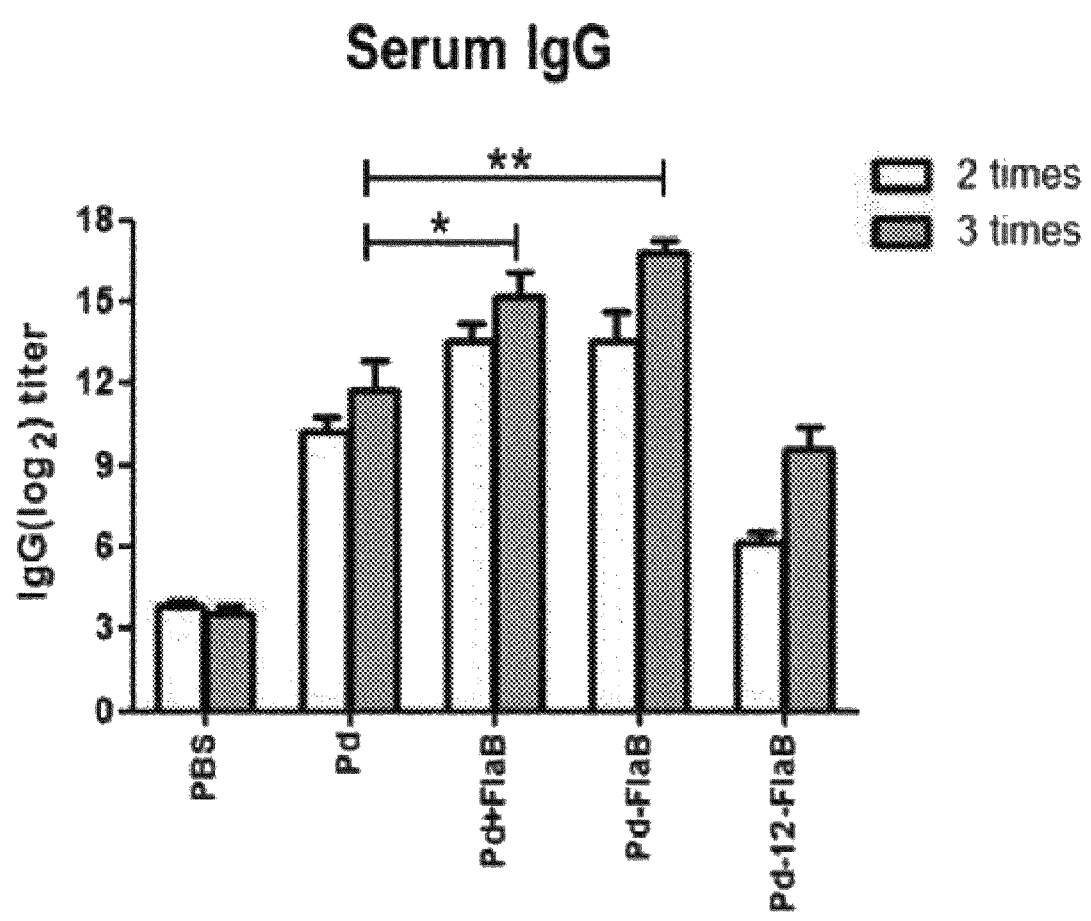
FIG. 18 shows serum IgG titer by immunization of Pd-FlaB recombinant protein.
Figure 19:
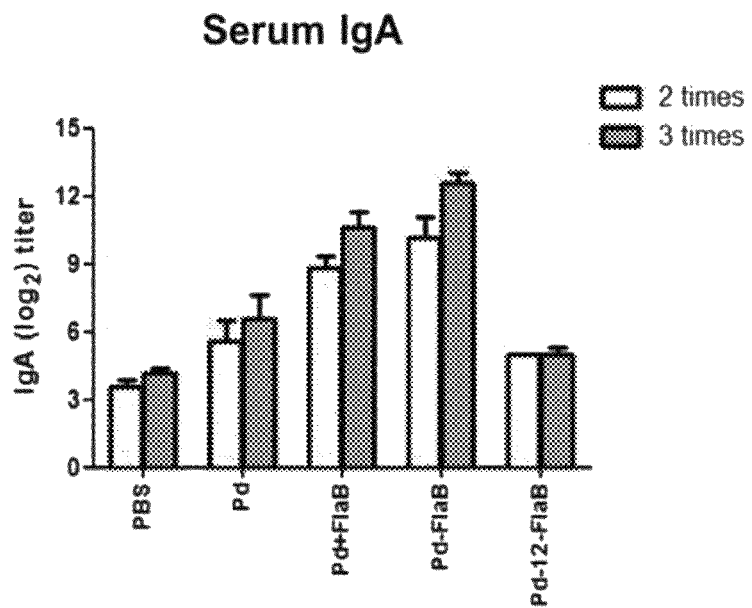
FIG. 19 shows serum IgA titer by immunization of Pd-FlaB recombinant protein.
Figure 20:
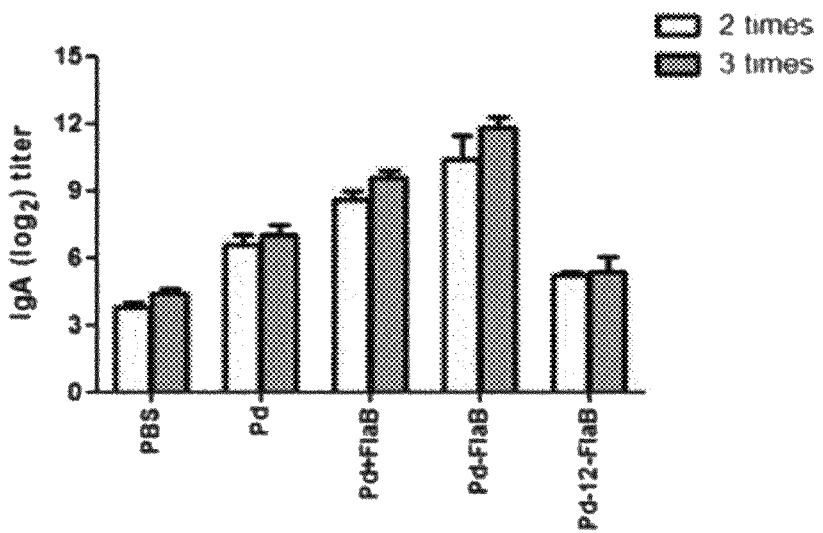
FIG. 20 shows fecal IgG titer by immunization of Pd-FlaB recombinant protein.

For the verification of vaccine efficacy of the prepared Pd and FlaB-Pd proteins, 6-week-old female Balb/c mice purchased from Orient were used.

Following the schedule shown in FIG. 15, Pd (1 μg), FlaB (1.2 μg)+Pd (1.2 μg) mix, and FlaB-Pd (2.2 μg) fusion protein were intranasally administered to mice three times. After 7 days of the last administration, the whole blood of the mice was obtained, and then serum was isolated.

FIG. 16 shows that a structure recognizing antibody was not produced merely when the norovirus Pd antigen was administered in mixing with FlaB, but a structure recognizing antibody, which did not recognize a monomer only when immunization was conducted using recombinant FlaB-Pd protein and responded to an antigen on a dot blot experiment using a cell lysate with an antigen structure maintained, was produced. This indicates that some antigens need to have special antigen structures through protein engineering.

③ Electron Microscopic Observation

After the recombinant norovirus P domain protein and FlaB-P domain fusion were respectively purified, samples were stained with uranyl acetate, and then 2 μl of each sample was dropped on a carbon grid, followed by drying, and then was observed at an accelerated voltage of 30 kV using JEOL JEM-2100F transmission electron microscope. As a result, the formation of virus-like particle (VLP) structures is observed in the norovirus P domain recombinant protein. In the FlaB-P domain fusion protein, VLP forms were observed while a structure of aggregation of the VLP forms as subunits was observed (FIG. 17).

④ Observation of IgG and IgA Titers

Following the schedule shown in FIG. 15, a recombinant P domain antigen alone, FlaB and P domain mix, and a FlaB-P domain fusion protein vaccine were administered to 6-week-old female BalB/c mice three through the nasal cavity. After three times immunization, the whole blood (FIG. 18: serum IgG, FIG. 19: serum IgA) and feces (FIG. 20: fecal secretary IgA titer measurement) of the mice were collected, followed by serum isolation, and then an antigen-specific antibody titer using the recombinant P domain protein as an antigen was checked by using ELISA (secondary IgG antibody; Goat Anti-Mouse IgG, Human ads-HRP Cat. No. 1030-05, SouthemBiotech, Birmingham, Ala. 35260, USA: secondary IgA antibody; Goat Anti-Mouse IgA-HRP Cat. No. 1040-05, SouthemBiotech, Birmingham, Ala. 35260, USA) (FIGS. 18 to 20). As a result, it could be verified that the antigen-specific antibody titer was significantly increased in the FlaB+P domain mix administration group and the FlaB-P domain fusion vaccine administration group rather than in the P domain alone administration group.

What is claimed is:

1. A composition containing a recombinant protein comprising:
    (a) a repeated domain (RD) of tau (τ) protein; and
    (b) FlaB protein derived from *Vibrio vulnificus*,
    wherein the FlaB protein has the amino acid sequence of SEQ ID NO: 2.

2. The composition of claim 1, wherein the RD has the amino acid sequence of SEQ ID NO: 3.

3. The composition of claim 1, wherein the RD is encoded by the nucleotide sequence of SEQ ID NO: 5, which is a codon-optimized nucleotide sequence for expression in *E. coli*.

* * * * *

```
                        SEQUENCE LISTING

<160> NUMBER OF SEQ ID NOS: 17

<210> SEQ ID NO 1
<211> LENGTH: 1134
<212> TYPE: DNA
<213> ORGANISM: Vibrio vulnificus

<400> SEQUENCE: 1
atggcagtga atgtaaatac aaacgtagca gcaatgacag cacagcgtta cctgaataac     60
gcaaacagcg cacaacaaac ttcgatggag cgtctgtctt caggtttcaa atcaacagt    120 gcaaaagatg acgcagccgg tctgcaaatc tctaaccgct tgaacgtaca agtcgcggt    180 ctagacgttg cggtacgtaa cgccaacgac ggtatctcaa tcgcacaaac cgcagaaggt    240
gcgatgaaca gaccaccaa catcctacaa cgtatgcgtg acctatctct acaatccgcg     300
aacggctcaa actcaaaatc agagcgcgtg gcgattcaag aagaagtgac agcattgaat    360
gacgagctaa accgtattgc agaaaccacg tcttttggtg gtaacaagct gctaaacggt    420
acttacggca cgaaagcaat gcaaattggt gcggataacg gtgaagcggt catgctttca    480
ctgaaagaca tgcgctctga caacgtgatg atgggcggcg tgagctacca agctgaagaa    540
ggcaaagaca agaactggaa tgtggccgca ggcgacaacg acttgacgat tgcactgaca    600
gacagctttg gtaacgagca agagatcgaa atcaacgcga aagcgggtga tgacatcgaa    660
gagctagcga cgtacatcaa cggtcaaact gaccttgtaa aagcgtcagt gggtgaaggc    720
ggcaagctac agatctttgc tggtaacaac aaagttcaag gtgaaattgc tttctcaggt    780
agcctagctg gtgaacttgg cctaggcgaa ggcaaaaacg tcacggtaga cacgattgac    840
gtgacaaccg tacaaggtgc gcaagagtcg gtagcgattg tggatgcggc actgaaatac    900
gtagacagcc accgtgcaga gctgggtgca ttccagaacc gtttcaacca tgcaatcagc    960
aacttggaca acatcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa         1134

<210> SEQ ID NO 2
<211> LENGTH: 380
<212> TYPE: PRT
<213> ORGANISM: Vibrio vulnificus

<400> SEQUENCE: 2

Asn Val Asp Met Ala Val Asn Val Asn Thr Asn Val Ala Ala Met Thr
  1               5                  10                  15

Ala Gln Arg Tyr Leu Asn Asn Ala Asn Ser Ala Gln Gln Thr Ser Met
             20                  25                  30

Glu Arg Leu Ser Ser Gly Phe Lys Ile Asn Ser Ala Lys Asp Asp Ala
         35                  40                  45

Ala Gly Leu Gln Ile Ser Asn Arg Leu Asn Val Gln Ser Arg Gly Leu
     50                  55                  60

Asp Val Ala Val Arg Asn Ala Asn Asp Gly Ile Ser Ile Ala Gln Thr
 65                  70                  75                  80

Ala Glu Gly Ala Met Asn Glu Thr Thr Asn Ile Leu Gln Arg Met Arg
                 85                  90                  95
```

```
Asp Leu Ser Leu Gln Ser Ala Asn Gly Ser Asn Ser Lys Ser Glu Arg
            100                 105                 110

Val Ala Ile Gln Glu Glu Val Thr Ala Leu Asn Asp Glu Leu Asn Arg
        115                 120                 125

Ile Ala Glu Thr Thr Ser Phe Gly Gly Asn Lys Leu Leu Asn Gly Thr
    130                 135                 140

Tyr Gly Thr Lys Ala Met Gln Ile Gly Ala Asp Asn Gly Glu Ala Val
145                 150                 155                 160

Met Leu Ser Leu Lys Asp Met Arg Ser Asp Asn Val Met Met Gly Gly
                165                 170                 175

Val Ser Tyr Gln Ala Glu Glu Gly Lys Asp Lys Asn Trp Asn Val Ala
            180                 185                 190

Ala Gly Asp Asn Asp Leu Thr Ile Ala Leu Thr Asp Ser Phe Gly Asn
        195                 200                 205

Glu Gln Glu Ile Glu Ile Asn Ala Lys Ala Gly Asp Asp Ile Glu Glu
    210                 215                 220

Leu Ala Thr Tyr Ile Asn Gly Gln Thr Asp Leu Val Lys Ala Ser Val
225                 230                 235                 240

Gly Glu Gly Gly Lys Leu Gln Ile Phe Ala Gly Asn Asn Lys Val Gln
                245                 250                 255

Gly Glu Ile Ala Phe Ser Gly Ser Leu Ala Gly Glu Leu Gly Leu Gly
            260                 265                 270

Glu Gly Lys Asn Val Thr Val Asp Thr Ile Asp Val Thr Thr Val Gln
        275                 280                 285

Gly Ala Gln Glu Ser Val Ala Ile Val Asp Ala Ala Leu Lys Tyr Val
    290                 295                 300

Asp Ser His Arg Ala Glu Leu Gly Ala Phe Gln Asn Arg Phe Asn His
305                 310                 315                 320

Ala Ile Ser Asn Leu Asp Asn Ile Asn Glu Asn Val Asn Ala Ser Lys
                325                 330                 335

Ser Arg Ile Lys Asp Thr Asp Phe Ala Lys Glu Thr Thr Gln Leu Thr
            340                 345                 350

Lys Thr Gln Ile Leu Ser Gln Ala Ser Ser Ser Ile Leu Ala Gln Ala
        355                 360                 365

Lys Gln Ala Pro Asn Ser Ala Leu Ser Leu Leu Gly
    370                 375                 380

<210> SEQ ID NO 3
<211> LENGTH: 126
<212> TYPE: PRT
<213> ORGANISM: homo sapiens

<400> SEQUENCE: 3

Leu Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Gly Lys
            20                  25                  30

Val Gln Ile Ile Asn Lys Lys Leu Asp Leu Ser Asn Val Gln Ser Lys
        35                  40                  45

Cys Gly Ser Lys Asp Asn Ile Lys His Val Pro Gly Gly Gly Ser Val
    50                  55                  60

Gln Ile Val Tyr Lys Pro Val Asp Leu Ser Lys Val Thr Ser Lys Cys
65                  70                  75                  80

Gly Ser Leu Gly Asn Ile His His Lys Pro Gly Gly Gly Gln Val Glu
                85                  90                  95
```

Val Lys Ser Glu Lys Leu Asp Phe Lys Asp Arg Val Gln Ser Lys Ile
                100                 105                 110

Gly Ser Leu Asp Asn Ile Thr His Val Pro Gly Gly Asn
            115                 120                 125

<210> SEQ ID NO 4
<211> LENGTH: 378
<212> TYPE: DNA
<213> ORGANISM: homo sapiens

<400> SEQUENCE: 4
ctgcagacag cccccgtgcc catgccagac ctgaagaatg tcaagtccaa gatcggctcc      60
actgagaacc tgaagcacca gccgggaggc gggaaggtgc agataattaa taagaagctg     120
gatcttagca acgtccagtc caagtgtggc tcaaaggata tatcaaaaca cgtcccggga     180
ggcggcagtg tgcaaatagt ctacaaacca gttgacctga gcaaggtgac ctccaagtgt     240
ggctcattag caacatcca tcataaacca ggaggtggcc aggtggaagt aaaatctgag     300
aagcttgact tcaaggacag agtccagtcg aagattgggt ccctggacaa tatcacccac     360
gtccctggcg aggaaat                                                    378

<210> SEQ ID NO 5
<211> LENGTH: 378
<212> TYPE: DNA
<213> ORGANISM: Artificial Sequence
<220> FEATURE:
<223> OTHER INFORMATION: codon optimized TauRD

<400> SEQUENCE: 5
ctgcagacag cccccgtgcc catgccagac ctgaagaatg tcaagtccaa gatcggctcc      60
actgagaacc tgaagcacca gccgggaggc gggaaggtgc agataattaa taagaagctg     120
gatcttagca acgtccagtc caagtgtggc tcaaaggata tatcaaaaca cgtcccggga     180
ggcggcagtg tgcaaatagt ctacaaacca gttgacctga gcaaggtgac ctccaagtgt     240
ggctcattag caacatcca tcataaacca ggaggtggcc aggtggaagt aaaatctgag     300
aagcttgact tcaaggacag agtccagtcg aagattgggt ccctggacaa tatcacccac     360
gtccctggcg aggaaat                                                    378

<210> SEQ ID NO 6
<211> LENGTH: 1519
<212> TYPE: DNA
<213> ORGANISM: Artificial Sequence
<220> FEATURE:
<223> OTHER INFORMATION: FlaB-TauRD

<400> SEQUENCE: 6
tggcagtgaa tgtaaataca acgtagcag caatgacagc acagcgttac ctgaataacg      60
caaacagcgc acaacaaact tcgatggagc gtctgtcttc aggtttcaaa atcaacagtg     120
caaaagatga cgcagccggt ctgcaaatct ctaaccgctt gaacgtacaa agtcgcggtc     180
tagacgttgc ggtacgtaac gccaacgacg gtatctcaat cgcacaaacc gcagaaggtg     240
cgatgaacga gaccaccaac atcctacaac gtatgcgtga cctatctcta caatccgcga     300
acggctcaaa ctcaaaatca gagcgcgtgg cgattcaaga agaagtgaca gcattgaatg     360
acgagctaaa ccgtattgca gaaaccacgt cttttggtgg taacaagctg ctaaacggta     420
cttacggcac gaaagcaatg caaattggtg cggataacgg tgaagcggtc atgctttcac     480

```
tgaaagacat gcgctctgac aacgtgatga tgggcggcgt gagctaccaa gctgaagaag      540
gcaaagacaa gaactggaat gtggccgcag gcgacaacga cttgacgatt gcactgacag      600
acagctttgg taacgagcaa gagatcgaaa tcaacgcgaa agcgggtgat gacatcgaag      660
agctagcgac gtacatcaac ggtcaaactg accttgtaaa agcgtcagtg ggtgaaggcg      720
gcaagctaca gatctttgct ggtaacaaca aagttcaagg tgaaattgct ttctcaggta      780
gcctagctgg tgaacttggc ctaggcgaag gcaaaaacgt cacggtagac acgattgacg      840
tgacaaccgt acaaggtgcg caagagtcgg tagcgattgt ggatgcggca ctgaaatacg      900
tagacagcca ccgtgcagag ctgggtgcat tccagaaccg tttcaaccat gcaatcagca      960
acttggacaa catcaacgaa aacgtgaacg cgtcgaagag ccgaatcaaa gataccgact     1020
tcgcgaaaga aacgactcag ttgaccaaga cacaaattct atcgcaagca tcaagttcca     1080
ttcttgcgca agcgaaacaa gcgccaaact cagcgctaag tctactaggc ttaagtcgac     1140
actgcaaaca gccccggttc ctatgcccga tctgaagaat gtgaaatcta aataggctc     1200 gactgaaaat ctgaaacacc aacctggtgg tggtaaagtg cagattatca acaaaaaatt     1260
ggacctgtca aatgtacaga gtaagtgtgg ttccaaagat aacatcaaac atgttccggg     1320
gggcgggtcc gtacagattg tgtataagcc agtcgatctg agcaaagtca ccagcaaatg     1380
cgggtctctg gcaacattc atcacaaacc aggcggtgga caggttgagg tcaagagcga     1440
aaagctggac tttaaggacc gtgttcagag taaaatcggc tcactcgata acattacgca     1500
tgtgccggga ggaggtaat                                                 1519
```

<210> SEQ ID NO 7
<211> LENGTH: 506
<212> TYPE: PRT
<213> ORGANISM: Artificial Sequence
<220> FEATURE:
<223> OTHER INFORMATION: FlaB-TauRD

<400> SEQUENCE: 7

```
Asn Val Asp Met Ala Val Asn Val Asn Thr Asn Val Ala Ala Met Thr
1               5                   10                  15

Ala Gln Arg Tyr Leu Asn Asn Ala Asn Ser Ala Gln Gln Thr Ser Met
            20                  25                  30

Glu Arg Leu Ser Ser Gly Phe Lys Ile Asn Ser Ala Lys Asp Asp Ala
        35                  40                  45

Ala Gly Leu Gln Ile Ser Asn Arg Leu Asn Val Gln Ser Arg Gly Leu
    50                  55                  60

Asp Val Ala Val Arg Asn Ala Asn Asp Gly Ile Ser Ile Ala Gln Thr
65                  70                  75                  80

Ala Glu Gly Ala Met Asn Glu Thr Thr Asn Ile Leu Gln Arg Met Arg
                85                  90                  95

Asp Leu Ser Leu Gln Ser Ala Asn Gly Ser Asn Ser Lys Ser Glu Arg
            100                 105                 110

Val Ala Ile Gln Glu Glu Val Thr Ala Leu Asn Asp Glu Leu Asn Arg
        115                 120                 125

Ile Ala Glu Thr Thr Ser Phe Gly Gly Asn Lys Leu Leu Asn Gly Thr
    130                 135                 140

Tyr Gly Thr Lys Ala Met Gln Ile Gly Ala Asp Asn Gly Glu Ala Val
145                 150                 155                 160

Met Leu Ser Leu Lys Asp Met Arg Ser Asp Asn Val Met Gly Gly
                165                 170                 175
```

Val Ser Tyr Gln Ala Glu Glu Gly Lys Asp Lys Asn Trp Asn Val Ala
            180                 185                 190

Ala Gly Asp Asn Asp Leu Thr Ile Ala Leu Thr Asp Ser Phe Gly Asn
        195                 200                 205

Glu Gln Glu Ile Glu Ile Asn Ala Lys Ala Gly Asp Asp Ile Glu Glu
    210                 215                 220

Leu Ala Thr Tyr Ile Asn Gly Gln Thr Asp Leu Val Lys Ala Ser Val
225                 230                 235                 240

Gly Glu Gly Gly Lys Leu Gln Ile Phe Ala Gly Asn Asn Lys Val Gln
                245                 250                 255

Gly Glu Ile Ala Phe Ser Gly Ser Leu Ala Gly Glu Leu Gly Leu Gly
            260                 265                 270

Glu Gly Lys Asn Val Thr Val Asp Thr Ile Asp Val Thr Thr Val Gln
        275                 280                 285

Gly Ala Gln Glu Ser Val Ala Ile Val Asp Ala Ala Leu Lys Tyr Val
    290                 295                 300

Asp Ser His Arg Ala Glu Leu Gly Ala Phe Gln Asn Arg Phe Asn His
305                 310                 315                 320

Ala Ile Ser Asn Leu Asp Asn Ile Asn Glu Asn Val Asn Ala Ser Lys
                325                 330                 335

Ser Arg Ile Lys Asp Thr Asp Phe Ala Lys Glu Thr Thr Gln Leu Thr
            340                 345                 350

Lys Thr Gln Ile Leu Ser Gln Ala Ser Ser Ile Leu Ala Gln Ala
        355                 360                 365

Lys Gln Ala Pro Asn Ser Ala Leu Ser Leu Leu Gly Leu Gln Thr Ala
    370                 375                 380

Pro Val Pro Met Pro Asp Leu Lys Asn Val Lys Ser Lys Ile Gly Ser
385                 390                 395                 400

Thr Glu Asn Leu Lys His Gln Pro Gly Gly Lys Val Gln Ile Ile
                405                 410                 415

Asn Lys Lys Leu Asp Leu Ser Asn Val Gln Ser Lys Cys Gly Ser Lys
            420                 425                 430

Asp Asn Ile Lys His Val Pro Gly Gly Gly Ser Val Gln Ile Val Tyr
        435                 440                 445

Lys Pro Val Asp Leu Ser Lys Val Thr Ser Lys Cys Gly Ser Leu Gly
    450                 455                 460

Asn Ile His His Lys Pro Gly Gly Gly Gln Val Glu Val Lys Ser Glu
465                 470                 475                 480

Lys Leu Asp Phe Lys Asp Arg Val Gln Ser Lys Ile Gly Ser Leu Asp
                485                 490                 495

Asn Ile Thr His Val Pro Gly Gly Gly Asn
            500                 505

<210> SEQ ID NO 8
<211> LENGTH: 28
<212> TYPE: DNA
<213> ORGANISM: Artificial Sequence
<220> FEATURE:
<223> OTHER INFORMATION: Forward primer for flaB

<400> SEQUENCE: 8
gaattcatgg cagtgaatgt aaatacaa                                      28

<210> SEQ ID NO 9
<211> LENGTH: 27
<212> TYPE: DNA

```
<213> ORGANISM: Artificial Sequence
<220> FEATURE:
<223> OTHER INFORMATION: Reverse primer for flaB

<400> SEQUENCE: 9
ctgcagttag cctagtagac ttagcgc                                               27

<210> SEQ ID NO 10
<211> LENGTH: 26
<212> TYPE: DNA
<213> ORGANISM: Artificial Sequence
<220> FEATURE:
<223> OTHER INFORMATION: Forward primer for TauRD

<400> SEQUENCE: 10
gaattcctgc aaacagcccc ggttcc                                                26

<210> SEQ ID NO 11
<211> LENGTH: 26
<212> TYPE: DNA
<213> ORGANISM: Artificial Sequence
<220> FEATURE:
<223> OTHER INFORMATION: Reverse primer for TauRD

<400> SEQUENCE: 11
ctcgagatta cctcctcccg gcacat                                                26

<210> SEQ ID NO 12
<211> LENGTH: 957
<212> TYPE: DNA
<213> ORGANISM: Unknown
<220> FEATURE:
<223> OTHER INFORMATION: Norovirus

<400> SEQUENCE: 12
tcaagaacta aaccattcac cgtcccgatc ttaactgttg aggaaatgtc caactcaaga          60
ttccccattc ctttggaaaa gttgtacacg ggtcccagca gtgcttttgt tgtccaacca         120
caaaatggca ggtgcacgac tgatggcgtg ctcttaggca ctacccagct gtctgctgtc         180
aatatctgca ccttcagagg ggatgtcacc cacattgcag gcagtcatga ctatataatg         240
aatttggctt ctcaaaattg aacaattat gacccaacag aagaaatccc agcccctctg         300
ggaactccag atttcgtggg aaagatccaa ggcatgctca cccaaaccac aagagaggat         360
ggctcgaccc gcgcccacaa agctacagtg agcactggga gcgtccactt cactccaaag         420
ttgggcagtg ttcaatacac cactgacaca acaatgatc ttcaaactgg ccaaaacacg         480
aaattcaccc cagtcggcgt catccaggat ggtaataacc accaaaatga accccagcaa         540
tgggtactcc caaattactc aggtagaact ggtcataatg tgcacctagc tcctgccgtt         600
gccccacttt tcccaggcga gcaacttctc ttctttaggt ccactatgcc cggggtgtagc        660
gggtatccca acatgaatct ggattgccta ctccccagg aatgggtgca gcacttctac         720
caagaagcag ctccagcaca atctgatgtg gctctgctga gatttgtgaa tccagacaca         780
ggtagggttc tgtttgagtg caagctccat aaatcaggct atgtcacagt ggctcacact         840
ggcccgcatg atttggttat ccccccaat ggttatttta gatttgattc ctgggtcaac         900
cagttctaca cacttgcccc catgggaaat ggagcggggc gcagacgtgc attataa           957

<210> SEQ ID NO 13
<211> LENGTH: 319
<212> TYPE: PRT
<213> ORGANISM: Unknown
```

<220> FEATURE:
<223> OTHER INFORMATION: Norovirus

<400> SEQUENCE: 13

Met Ser Arg Thr Lys Pro Phe Thr Val Pro Ile Leu Thr Val Glu Glu
1               5                   10                  15

Met Ser Asn Ser Arg Phe Pro Ile Pro Leu Glu Lys Leu Tyr Thr Gly
            20                  25                  30

Pro Ser Ser Ala Phe Val Val Gln Pro Gln Asn Gly Arg Cys Thr Thr
        35                  40                  45

Asp Gly Val Leu Leu Gly Thr Thr Gln Leu Ser Ala Val Asn Ile Cys
    50                  55                  60

Thr Phe Arg Gly Asp Val Thr His Ile Ala Gly Ser His Asp Tyr Ile
65                  70                  75                  80

Met Asn Leu Ala Ser Gln Asn Trp Asn Asn Tyr Asp Pro Thr Glu Glu
                85                  90                  95

Ile Pro Ala Pro Leu Gly Thr Pro Asp Phe Val Gly Lys Ile Gln Gly
            100                 105                 110

Met Leu Thr Gln Thr Thr Arg Glu Asp Gly Ser Thr Arg Ala His Lys
        115                 120                 125

Ala Thr Val Ser Thr Gly Ser Val His Phe Thr Pro Lys Leu Gly Ser
    130                 135                 140

Val Gln Tyr Thr Thr Asp Thr Asn Asn Asp Leu Gln Thr Gly Gln Asn
145                 150                 155                 160

Thr Lys Phe Thr Pro Val Gly Val Ile Gln Asp Gly Asn Asn His Gln
                165                 170                 175

Asn Glu Pro Gln Gln Trp Val Leu Pro Asn Tyr Ser Gly Arg Thr Gly
            180                 185                 190

His Asn Val His Leu Ala Pro Ala Val Ala Pro Thr Phe Pro Gly Glu
        195                 200                 205

Gln Leu Leu Phe Phe Arg Ser Thr Met Pro Gly Cys Ser Gly Tyr Pro
    210                 215                 220

Asn Met Asn Leu Asp Cys Leu Leu Pro Gln Glu Trp Val Gln His Phe
225                 230                 235                 240

Tyr Gln Glu Ala Ala Pro Ala Gln Ser Asp Val Ala Leu Leu Arg Phe
                245                 250                 255

Val Asn Pro Asp Thr Gly Arg Val Leu Phe Glu Cys Lys Leu His Lys
            260                 265                 270

Ser Gly Tyr Val Thr Val Ala His Thr Gly Pro His Asp Leu Val Ile
        275                 280                 285

Pro Pro Asn Gly Tyr Phe Arg Phe Asp Ser Trp Val Asn Gln Phe Tyr
    290                 295                 300

Thr Leu Ala Pro Met Gly Asn Gly Ala Gly Arg Arg Arg Ala Leu
305                 310                 315

<210> SEQ ID NO 14
<211> LENGTH: 2097
<212> TYPE: DNA
<213> ORGANISM: Artificial Sequence
<220> FEATURE:
<223> OTHER INFORMATION: Pd-flaB

<400> SEQUENCE: 14
atgtcaagaa ctaaaccatt caccgtcccg atcttaactg ttgaggaaat gtccaactca      60
agattcccca ttcctttgga aaagttgtac acgggtccca gcagtgcttt tgttgtccaa     120

| | | | | |
|---|---|---|---|---|
| ccacaaaatg | gcaggtgcac | gactgatggc | gtgctcttag | gcactaccca gctgtctgct | 180 |
| gtcaatatct | gcaccttcag | aggggatgtc | acccacattg | caggcagtca tgactatata | 240 |
| atgaatttgg | cttctcaaaa | ttggaacaat | tatgacccaa | cagaagaaat cccagcccct | 300 |
| ctgggaactc | cagatttcgt | gggaaagatc | aaggcatgc | tcacccaaac cacaagagag | 360 |
| gatggctcga | cccgcgccca | caaagctaca | gtgagcactg | gagcgtcca cttcactcca | 420 |
| aagttgggca | gtgttcaata | caccactgac | acaaacaatg | atcttcaaac tggccaaaac | 480 |
| acgaaattca | ccccagtcgg | cgtcatccag | gatggtaata | ccaccaaaa tgaaccccag | 540 |
| caatgggtac | tcccaaatta | ctcaggtaga | actggtcata | atgtgcacct agctcctgcc | 600 |
| gttgccccca | ctttcccagg | cgagcaactt | ctcttcttta | ggtccactat gcccgggtgt | 660 |
| agcgggtatc | ccaacatgaa | tctggattgc | ctactccccc | aggaatgggt gcagcacttc | 720 |
| taccaagaag | cagctccagc | acaatctgat | gtggctctgc | tgagatttgt gaatccagac | 780 |
| acaggtaggg | ttctgtttga | gtgcaagctc | cataaatcag | gctatgtcac agtggctcac | 840 |
| actggcccgc | atgatttggt | tatcccccc | aatggttatt | ttagatttga ttcctgggtc | 900 |
| aaccagttct | acacacttgc | ccccatggga | aatggagcgg | ggcgcagacg tgcattagtc | 960 |
| gacatggcag | tgaatgtaaa | tacaaacgta | gcagcaatga | cagcacagcg ttacctgaat | 1020 |
| aacgcaaaca | gcgcacaaca | aacttcgatg | gagcgtctgt | cttcaggttt caaaatcaac | 1080 |
| agtgcaaaag | atgacgcagc | cggtctgcaa | atctctaacc | gcttgaacgt acaaagtcgc | 1140 |
| ggtctagacg | ttgcggtacg | taacgccaac | gacggtatct | caatcgcaca aaccgcagaa | 1200 |
| ggtgcgatga | cgagaccac | caacatccta | caacgtatgc | gtgacctatc tctacaatcc | 1260 |
| gcgaacggct | caaactcaaa | atcagagcgc | gtggcgattc | aagaagaagt gacagcattg | 1320 |
| aatgacgagc | taaccgtat | tgcagaaacc | acgtctttg | gtggtaacaa gctgctaaac | 1380 |
| ggtacttacg | gcacgaaagc | aatgcaaatt | ggtgcggata | cggtgaagc ggtcatgctt | 1440 |
| tcactgaaag | acatgcgctc | tgacaacgtg | atgatgggcg | gcgtgagcta ccaagctgaa | 1500 |
| gaaggcaaag | acaagaactg | gaatgtggcc | gcaggcgaca | acgacttgac gattgcactg | 1560 |
| acagacagct | ttggtaacga | gcaagagatc | gaaatcaacg | cgaaagcggg tgatgacatc | 1620 |
| gaagagctag | cgacgtacat | caacggtcaa | actgaccttg | taaaagcgtc agtgggtgaa | 1680 |
| ggcggcaagc | tacagatctt | tgctggtaac | aacaaagttc | aaggtgaaat tgctttctca | 1740 |
| ggtagcctag | ctggtgaact | tggcctaggc | gaaggcaaaa | acgtcacggt agacacgatt | 1800 |
| gacgtgacaa | ccgtacaagg | tgcgcaagag | tcggtagcga | ttgtggatgc ggcactgaaa | 1860 |
| tacgtagaca | gccaccgtgc | agagctgggt | gcattccaga | accgtttcaa ccatgcaatc | 1920 |
| agcaacttgg | acaacatcaa | cgaaaacgtg | aacgcgtcga | agagccgaat caaagatacc | 1980 |
| gacttcgcga | agaaacgac | tcagttgacc | aagacacaaa | ttctatcgca agcatcaagt | 2040 |
| tccattcttg | cgcaagcgaa | acaagcgcca | aactcagcgc | taagtctact aggctaa | 2097 |

<210> SEQ ID NO 15
<211> LENGTH: 699
<212> TYPE: PRT
<213> ORGANISM: Artificial Sequence
<220> FEATURE:
<223> OTHER INFORMATION: Pd-flaB

<400> SEQUENCE: 15

```
Asn Val Asp Met Ala Val Asn Val Asn Thr Asn Val Ala Ala Met Thr
1               5                   10                  15
```

```
Ala Gln Arg Tyr Leu Asn Asn Ala Asn Ser Ala Gln Thr Ser Met
            20                  25                  30

Glu Arg Leu Ser Ser Gly Phe Lys Ile Asn Ser Ala Lys Asp Asp Ala
            35                  40                  45

Ala Gly Leu Gln Ile Ser Asn Arg Leu Asn Val Gln Ser Arg Gly Leu
 50                  55                  60

Asp Val Ala Val Arg Asn Ala Asn Asp Gly Ile Ser Ile Ala Gln Thr
 65                  70                  75                  80

Ala Glu Gly Ala Met Asn Glu Thr Thr Asn Ile Leu Gln Arg Met Arg
                 85                  90                  95

Asp Leu Ser Leu Gln Ser Ala Asn Gly Ser Asn Ser Lys Ser Glu Arg
             100                 105                 110

Val Ala Ile Gln Glu Glu Val Thr Ala Leu Asn Asp Glu Leu Asn Arg
             115                 120                 125

Ile Ala Glu Thr Thr Ser Phe Gly Gly Asn Lys Leu Leu Asn Gly Thr
 130                 135                 140

Tyr Gly Thr Lys Ala Met Gln Ile Gly Ala Asp Asn Gly Glu Ala Val
145                 150                 155                 160

Met Leu Ser Leu Lys Asp Met Arg Ser Asp Asn Val Met Met Gly Gly
                 165                 170                 175

Val Ser Tyr Gln Ala Glu Gly Lys Asp Lys Asn Trp Asn Val Ala
             180                 185                 190

Ala Gly Asp Asn Asp Leu Thr Ile Ala Leu Thr Asp Ser Phe Gly Asn
             195                 200                 205

Glu Gln Glu Ile Glu Ile Asn Ala Lys Ala Gly Asp Asp Ile Glu Glu
210                 215                 220

Leu Ala Thr Tyr Ile Asn Gly Gln Thr Asp Leu Val Lys Ala Ser Val
225                 230                 235                 240

Gly Glu Gly Gly Lys Leu Gln Ile Phe Ala Gly Asn Asn Lys Val Gln
                 245                 250                 255

Gly Glu Ile Ala Phe Ser Gly Ser Leu Ala Gly Glu Leu Gly Leu Gly
             260                 265                 270

Glu Gly Lys Asn Val Thr Val Asp Thr Ile Asp Val Thr Thr Val Gln
             275                 280                 285

Gly Ala Gln Glu Ser Val Ala Ile Val Asp Ala Ala Leu Lys Tyr Val
 290                 295                 300

Asp Ser His Arg Ala Glu Leu Gly Ala Phe Gln Asn Arg Phe Asn His
305                 310                 315                 320

Ala Ile Ser Asn Leu Asp Asn Ile Asn Glu Asn Val Asn Ala Ser Lys
                 325                 330                 335

Ser Arg Ile Lys Asp Thr Asp Phe Ala Lys Glu Thr Thr Gln Leu Thr
             340                 345                 350

Lys Thr Gln Ile Leu Ser Gln Ala Ser Ser Ser Ile Leu Ala Gln Ala
             355                 360                 365

Lys Gln Ala Pro Asn Ser Ala Leu Ser Leu Leu Gly Met Ser Arg Thr
 370                 375                 380

Lys Pro Phe Thr Val Pro Ile Leu Thr Val Glu Glu Met Ser Asn Ser
385                 390                 395                 400

Arg Phe Pro Ile Pro Leu Glu Lys Leu Tyr Thr Gly Pro Ser Ser Ala
                 405                 410                 415

Phe Val Val Gln Pro Gln Asn Gly Arg Cys Thr Thr Asp Gly Val Leu
             420                 425                 430

Leu Gly Thr Thr Gln Leu Ser Ala Val Asn Ile Cys Thr Phe Arg Gly
```

```
                    435                 440                 445
Asp Val Thr His Ile Ala Gly Ser His Asp Tyr Ile Met Asn Leu Ala
    450                 455                 460

Ser Gln Asn Trp Asn Asn Tyr Asp Pro Thr Glu Glu Ile Pro Ala Pro
465                 470                 475                 480

Leu Gly Thr Pro Asp Phe Val Gly Lys Ile Gln Gly Met Leu Thr Gln
                485                 490                 495

Thr Thr Arg Glu Asp Gly Ser Thr Arg Ala His Lys Ala Thr Val Ser
            500                 505                 510

Thr Gly Ser Val His Phe Thr Pro Lys Leu Gly Ser Val Gln Tyr Thr
        515                 520                 525

Thr Asp Thr Asn Asn Asp Leu Gln Thr Gly Gln Asn Thr Lys Phe Thr
    530                 535                 540

Pro Val Gly Val Ile Gln Asp Gly Asn Asn His Gln Asn Glu Pro Gln
545                 550                 555                 560

Gln Trp Val Leu Pro Asn Tyr Ser Gly Arg Thr Gly His Asn Val His
                565                 570                 575

Leu Ala Pro Ala Val Ala Pro Thr Phe Pro Gly Glu Gln Leu Leu Phe
            580                 585                 590

Phe Arg Ser Thr Met Pro Gly Cys Ser Gly Tyr Pro Asn Met Asn Leu
        595                 600                 605

Asp Cys Leu Leu Pro Gln Glu Trp Val Gln His Phe Tyr Gln Glu Ala
    610                 615                 620

Ala Pro Ala Gln Ser Asp Val Ala Leu Leu Arg Phe Val Asn Pro Asp
625                 630                 635                 640

Thr Gly Arg Val Leu Phe Glu Cys Lys Leu His Lys Ser Gly Tyr Val
                645                 650                 655

Thr Val Ala His Thr Gly Pro His Asp Leu Val Ile Pro Pro Asn Gly
            660                 665                 670

Tyr Phe Arg Phe Asp Ser Trp Val Asn Gln Phe Tyr Thr Leu Ala Pro
        675                 680                 685

Met Gly Asn Gly Ala Gly Arg Arg Ala Leu
    690                 695

<210> SEQ ID NO 16
<211> LENGTH: 28
<212> TYPE: DNA
<213> ORGANISM: Artificial Sequence
<220> FEATURE:
<223> OTHER INFORMATION: Forward primer for P domain

<400> SEQUENCE: 16
catatgtcaa gaactaaacc attcaccg                                          28

<210> SEQ ID NO 17
<211> LENGTH: 26
<212> TYPE: DNA
<213> ORGANISM: Artificial Sequence
<220> FEATURE:
<223> OTHER INFORMATION: Reverse primer for P domain

<400> SEQUENCE: 17
gtcgactaat gcacgtctgc gccccg                                            26
```